US009447418B2

(12) United States Patent
Bates et al.

(10) Patent No.: US 9,447,418 B2
(45) Date of Patent: Sep. 20, 2016

(54) PRO- AND ANTI-ANGIOGENIC TREATMENTS

(75) Inventors: David Bates, Bristol (GB); Steven James Harper, Bristol (GB); Dawid Grzegorz Nowak, Bristol (GB)

(73) Assignee: UNIVERSITY OF BRISTOL, Bristol (GB)

( * ) Notice: Subject to any disclaimer, the term of this patent is extended or adjusted under 35 U.S.C. 154(b) by 434 days.

(21) Appl. No.: 12/530,596

(22) PCT Filed: Mar. 10, 2008

(86) PCT No.: PCT/GB2008/000824
§ 371 (c)(1),
(2), (4) Date: Feb. 12, 2010

(87) PCT Pub. No.: WO2008/110777
PCT Pub. Date: Sep. 18, 2008

(65) Prior Publication Data
US 2010/0210527 A1  Aug. 19, 2010

(30) Foreign Application Priority Data
Mar. 9, 2007 (GB) .................... 0704678.2

(51) Int. Cl.
A61K 38/16 (2006.01)
C12N 15/113 (2010.01)
A61K 31/535 (2006.01)

(52) U.S. Cl.
CPC .......... *C12N 15/1136* (2013.01); *A61K 31/535* (2013.01); *C12N 2310/11* (2013.01); *C12N 2310/3233* (2013.01); *C12N 2320/33* (2013.01)

(58) Field of Classification Search
CPC ..................... A61K 31/535; C12N 15/1136
USPC ........ 514/1.1, 1.9, 7.6, 8.9, 13.3, 44 R, 44 A
See application file for complete search history.

(56) References Cited

U.S. PATENT DOCUMENTS

| 4,808,402 A | 2/1989 | Leibovich et al. ............ 424/423 |
| 5,147,854 A | 9/1992 | Newman ......................... 514/12 |
| 2005/0054036 A1* | 3/2005 | Bates et al. ................... 435/69.1 |

FOREIGN PATENT DOCUMENTS

| JP | 05-213772 | 8/1993 | ............. A61K 37/24 |
| WO | WO 02/06516 | 1/2002 | |
| WO | WO 02/32449 | 4/2002 | ............. A61K 38/30 |
| WO | WO 03/012105 | 2/2003 | ............. C12N 15/19 |

OTHER PUBLICATIONS

Witkowski et al.; Conversion of a beta-Ketoacyl Synthase to a Malonyl Decarboxylase by Replacement of the Active-Site Cysteine with Glutamine; Biochemistry 38:11643-11650, 1999.*
Seffernick et al.; Melamine Deaminase and Atrazine Chlorohydrolase: 98 Percent Identical but Functionally Different; J. Bacteriol. 183(8):2405-2410, 2001.*
Nowak et al.; Expression of pro- and anti-angiogenic isoforms of VEGF is differentially regulated by splicing and growth factors; Journal of Cell Science; vol. 121; pp. 3487-3495; published Oct. 15, 2008.*
Bachmann et al.; The Use of In Vitro Methods to Predict In Vivo Pharmacokinetics and Drug Interactions; Current Drug Metabolism; vol. 2, pp. 299-314 (2001).*
Patil et al.; DNA-based therapeutics and DNA delivery systems: a comprehensive review; The AAPS Journal, 7(1): Article 9, E61-E77, 2005.*
Asano-Kato, et al. (2005) "TGF-beta1, IL-1beta, and Th2 cytokines stimulate vascular endothelial growth factor production from conjunctival fibroblasts." *Exp Eye Res* 80:555-560.
Bates DO, et al. (2002) "VEGF165b, an inhibitory splice variant of vascular endothelial growth factor, is down-regulated in renal cell carcinoma." *Cancer Res* 62:4123-4131.
Bates DO, et al. (2006) "The endogenous anti-angiogenic family of splice variants of VEGF, VEGF xxxb, are down-regulated in preeclamptic placentae at term." *Clin Sci (Lond)* 110:575-585.
Caceres, et al. (2002) "Alternative splicing: multiple control mechanisms and involvement in human disease." *Trends Genet* 18:186-193.
Carmeliet P. (2000) "VEGF gene therapy: stimulating angiogenesis or angioma-genesis?" *Nat Med* 6:1102-1103.
Celletti, et al. (2001) "Vascular endothelial growth factor enhances atherosclerotic plaque progression." *Nat Med* 7:425-429.
Charnock-Jones, et al. (2000) "The effect of progestins on vascular endothelial growth factor, oestrogen receptor and progesterone receptor immunoreactivity and endothelial cell density in human endometrium." *Hum Reprod* 15(Suppl 3):85-95.
Cohen, et al. (2005) "Sam68-Like Mammalian Protein 2, Identified by Digital Differential Display as Expressed by Podocytes, Is Induced in Proteinuria and Involved in Splice Site Selection of Vascular Endothelial Growth Factor." *J Am Soc Nephrol* 16:1958-1965.
Cramer, et al. (1999) "Coupling of transcription with alternative splicing: RNA pol II promoters modulate SF2/ASF and 9G8 effects on an exonic splicing enhancer." *Mol Cell* 4:251-258.
Cui, et al. (2004) "Differentiated human podocytes endogenously express an inhibitory isoform of vascular endothelial growth factor (VEGF165b) mRNA and protein." *Am. J. Physiol. Renal Physiol.* 286:F767-F773.
Dowhan, et al. (2005) "Steroid hormone receptor coactivation and alternative RNA splicing by U2AF65-related proteins CAPERalpha and CAPERbeta." *Mol Cell* 17:429-439.

(Continued)

*Primary Examiner* — Antonio Galisteo Gonzalez
(74) *Attorney, Agent, or Firm* — Harness, Dickey & Pierce, P.L.C.

(57) ABSTRACT

The invention provides a method of selectively pro-orantiangiogenic treatment of a mammalian subject, comprising site-specific control of alternative splicing during processing of VEGF pre-mRNA transcribed from the C terminal exon 8 of the VEGF gene using controlling agents for the splicing, wherein one or more controlling agent which favors proximal splice site (PSS) splicing in said processing is used in the pro-angiogenic treatment and one or more controlling agent which favors distal splice site (DSS) splicing in said processing is used in the anti-angiogenic treatment.

5 Claims, 19 Drawing Sheets

(56) References Cited

OTHER PUBLICATIONS

Endo, et al. (1994) "Exclusion of an alternatively spliced exon in human ATP synthase gamma-subunit pre-mRNA requires de novo protein synthesis." *J Biol Chem* 269:12488-12493.
Eyetech (2003) "Anti-vascular endothelial growth factor therapy for subfoveal choroidal neovascularization secondary to age-related macular degeneration: phase II study results." *Ophthalmology* 110:979-986.
Ferrara, et al. (1997) "The biology of vascular endothelial growth factor." *Endocr Rev* 18:4-25.
Finkenzeller, et al. (1997) "Sp1 recognition sites in the proximal promoter of the human vascular endothelial growth factor gene are essential for platelet-derived growth factor-induced gene expression." *Oncogene* 15:669-676.
Folkman J. (1985) "Tumor angiogenesis." *Adv Cancer Res* 43:175-203.
Goad, et al. (1996) "Enhanced expression of vascular endothelial growth factor in human SaOS-2 osteoblast-like cells and murine osteoblasts induced by insulin-like growth factor I." *Endocrinology* 137:2262-2268.
Gragoudas, et al. (2004) "Pegaptanib for neovascular age-related macular degeneration." *N. Engl J Med* 351:2805-2816.
Hayes, et al. (2006) "Targeting the RNA splicing machinery as a novel treatment strategy for pancreatic carcinoma." *Cancer Res* 66:3819-3827.
Herrera, et al. (2001) "Activation of p38MAPK by TGF-beta in fetal rat hepatocytes requires radical oxygen production, but is dispensable for cell death." *Febs Lett* 499:225-229.
Hertel, et al. (1997) "Common themes in the function of transcription and splicing enhancers." *Curr Opin Cell Biol* 9:350-357.
Hirose, et al. (1999) "Phosphorylated RNA polymerase II stimulates pre-mRNA splicing." *Genes Dev* 13:1234-1239.
Houck, et al. (1991) "The vascular endothelial growth factor family: identification of a fourth molecular species and characterization of alternative splicing of RNA." *Mol Endocrinol* 5:1806-1814.
Hurwitz, et al. (2004) "Bevacizumab plus irinotecan, fluorouracil, and leucovorin for metastatic colorectal cancer." *N. Engl J Med* 350:2335-2342.
Idriss, et al. (1994) "Regulation of in vitro nucleic acid strand annealing activity of heterogeneous nuclear ribonucleoprotein protein A1 by reversible phosphorylation." *Biochemistry* 33:11382-11390.
Kalnina, et al. (2005) "Alterations of pre-mRNA splicing in cancer." *Genes Chromosomes Cancer* 42:342-357.
Koenigsberger, et al. (2000) "Differential regulation by multiple promoters of the gene encoding the neuron-restrictive silencer factor." *Proc Natl Acad Sci U S A* 97:2291-2296.
Kotsuji-Maruyama, et al. (2002) "PDGF-BB induces MAP kinase phosphorylation and VEGF expression in neurofibroma-derived cultured cells from patients with neurofibromatosis 1." *J Dermatol* 29:713-717.
Li, et al. (2004) "Possible participation of pICln in the regulation of angiogenesis through alternative splicing of vascular endothelial growth factor receptor mRNAs." *Endothelium* 11:293-300.
Li, et al. (1995) "Induction of vascular endothelial growth factor gene expression by interleukin-1 beta in rat aortic smooth muscle cells." *J Biol Chem* 270(1):308-312.
Lin, et al. (2007) "Cell stress modulates the function of splicing regulatory protein RBM4 in translation control." *Proc Natl Acad Sci U S A* 104:2235-2240.
Lynch, et al. (1996) "Assembly of specific SR protein complexes on distinct regulatory elements of the *Drosophila* doublesex splicing enhancer." *Genes Dev* 10:2089-2101.
Marzo, et al. (1997) "Antisense oligonucleotides specific for transforming growth factor β2 inhibit the growth of malignant mesothelioma both in vitro and in vivo." *Cancer Research* 57(15):3200-3207.
Matsumoto, et al. (1997) "Interleukin 10 and interleukin 13 synergize to inhibit vascular permeability factor release by peripheral blood mononuclear cells from patients with lipoid nephrosis." *Nephron* 77:212-218.

McCarthy M. (2003) "Antiangiogenesis drug promising for metastatic colorectal cancer." *Lancet* 361:1959.
Misteli, et al. (1997) "The dynamics of a pre-mRNA splicing factor in living cells." *Nature* 387:523-527.
Mukhopadhyay, et al. (1995) "Hypoxic induction of human vascular endothelial growth factor expression through c-Src activation." *Nature* 375:577-581.
Neufeld, et al. (1999) "Vascular endothelial growth factor (VEGF) and its receptors." *Faseb J* 13: 9-22, 1999.
Neufeld, et al. (1996) "Similarities and differences between the vascular endothelial growth factor (VEGF) splice variants." *Cancer and Metastasis Reviews* 15:153-158.
Nowak, et al. (2006) "Insulin-like growth factor-1 regulates alternative splicing of angiogenic and anti-angiogenic VEGF isoforms." *FASEB J.* 20:A538-A539 (Abstract Only).
Patterson, et al. (1996) "Downregulation of vascular endothelial growth factor receptors by tumor necrosis factor-alpha in cultured human vascular endothelial cells." *J Clin Invest* 98:490-496.
Perkett, et al. (1998) "Vascular endothelial growth factor expression is decreased in rat lung following exposure to 24 or 48 hours of hyperoxia: implications for endothelial cell survival." *Chest* 114:52S-53S.
Perrin, et al. (2005) "Diabetic retinopathy is associated with a switch in splicing from anti- to pro-angiogenic isoforms of vascular endothelial growth factor." *Diabetologia* 48:2422-2427.
Pertovaara, et al. (1994) "Vascular endothelial growth factor is induced in response to transforming growth factor-beta in fibroblastic and epithelial cells." *J Biol Chem* 269:6271-6274.
Rak, et al. (1995) "Mutant ras oncogenes upregulate VEGF/VPF expression: implications for induction and inhibition of tumor angiogenesis." *Cancer Res* 55:4575-4580.
Saleem, et al. (2002) "A conditionally immortalized human podocyte cell line demonstrating nephrin and podocin expression." *J Am Soc Nephrol* 13:630-638.
Shweiki, et al. (1992) "Vascular endothelial growth factor induced by hypoxia may mediate hypoxia-initiated angiogenesis." *Nature* 359:843-845.
Smith CW. (2005) "Alternative splicing—when two's a crowd." *Cell* 123:1-3.
Sone, et al. (1996) "Vascular endothelial growth factor is induced by long-term high glucose concentration and up-regulated by acute glucose deprivation in cultured bovine retinal pigmented epithelial cells." *Biochem Biophys Res Commun* 221:193-198.
Ueki, et al. (1992) "Excessive production of transforming growth-factor β1 can play an important role in the development of tumorigenesis by its action for angiogenesis: validity of neutralizing antibodies to block tumor growth." *Biochimica et Biophysica Acta* 1137(2):189-196.
Valcourt, et al. (2003) "Alternative splicing of type II procollagen pre-mRNA in chondrocytes is oppositely regulated by BMP-2 and TGF-beta1." *Febs Lett* 545:115-119.
van der Houven van Oordt, et al. (2000) "The MKK(3/6)-p38-signaling cascade alters the subcellular distribution of hnRNP A1 and modulates alternative splicing regulation." *J Cell Biol* 149:307-316.
Varey, et al. (2008) "VEGF$_{165}$b, an antiangiogenic VEGF-A isoform, binds and inhibits bevacizumab treatment in experimental colorectal carcinoma: balance of pro- and antiangiogenic VEGF-A isoforms has implications for therapy." *Br J Cancer* 98:1366-1379.
Venables JP. (2004) "Aberrant and alternative splicing in cancer." *Cancer Res* 64:7647-7654.
Woolard, et al. (2004) "VEGF165b, an inhibitory vascular endothelial growth factor splice variant: mechanism of action, in vivo effect on angiogenesis and endogenous protein expression." *Cancer Res.* 64:7822-7835.
Woolard, et al. (2006) "Splice factor regulation of alternative splicing of VEGF isoform families." *FASEB J.* 20(4):A539 (Abstract Only).
Yang, et al. (2003) "A randomized trial of bevacizumab, an anti-vascular endothelial growth factor antibody, for metastatic renal cancer." *N Engl J Med* 349:427-434.

(56) References Cited

OTHER PUBLICATIONS

Zhao, et al. (1995) "TGF-beta regulates expression of tenascin alternative-splicing isoforms in fetal rat lung." *Am J Physiol* 268:L173-180.

International Search Report (ISR) in PCT/GB2008/000824 dated Feb. 5, 2009.

Ghigna, et al. (1998) "Altered expression of heterogeneous nuclear ribonucleoproteins and SR factors in human colon adenocarcinomas[1]." *Cancer Research*, 58(24):5818-5824.

Amin, et al. (2011) WT1 mutants reveal SRPK1 to be a downstream angiogenesis target by altering VEGF splicing. *Cancer Cell* 20:768-780.

Fukuhara, et al. (2006) "Utilization of host SR protein kinases and RNA-splicing machinery during viral replication." *PNAS* 103(30):11329-11333.

Bain, et al. (2007) "The selectivity of protein kinase inhibitors: a further update." Biochem. J. 408:297-315.

European Office Action dated Nov. 17, 2014 in European Application No. 08718670.6.

\* cited by examiner

Effect of IGF-1 on expression of VEGF$_{xxx}$b and VEGF$_{xxx}$ proteins in A. RPE cells and B. Podocytes. IGF induced an upregulation of total VEGF but downregulated VEGF$_{xxx}$b., * $p<0.05$, ** $p<0.001$ vs respective control, one-way ANOVA, Dunnet's test, N=3

Effect of IGF-1 on expression of A. $VEGF_{165}b$ and B. $VEGF_{165/165b}$ in RPE cells. A reducing gel was used. Whereas VEGF165b protein was reduced by IGF, the total VEGF165 and VEGF165b combined did not reduce, and increased slightly Effect of TGF-β1 on expression of VEGF$_{xxx}$b and B. VEGF$_{total}$ in podocytes. A. ELISA of podocyte cell lysate shows that both VEGFxxxb and VEGFtotal were upregulated by TGF-β1. B. Non-reducing western blot demonstrating that the principal forms of VEGF$_{xxx}$b upregulated were VEGF$_{165}$b and VEGF$_{121}$b.

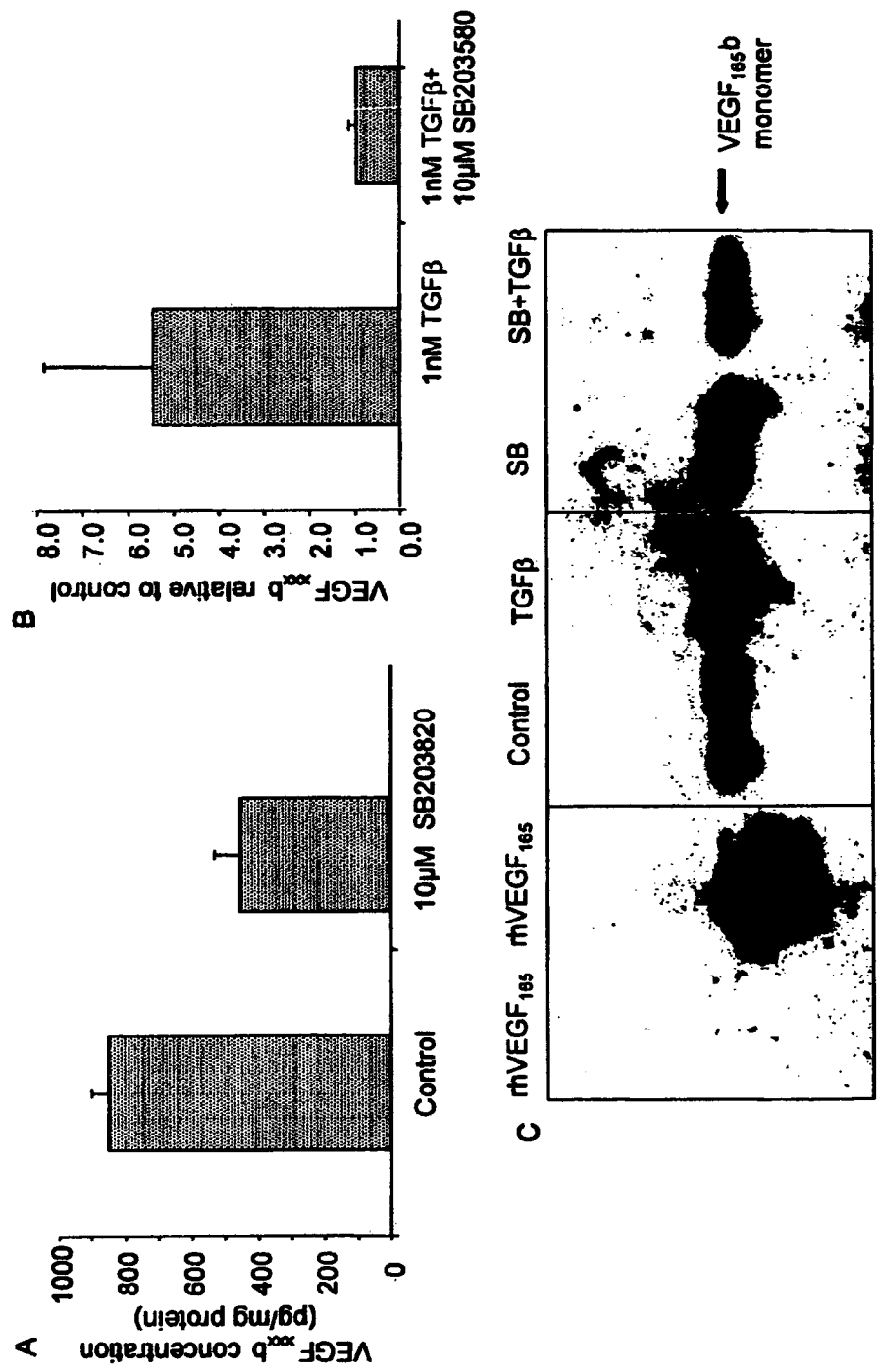

FIG. 5

P38-MAPK inhibition reduces distal splice site selection in the VEGF terminal exon. A. Treatment with the p38MAPK inhibitor SB203580 significantly reduced VEGF$_{xxx}$b in the supernatant of podocytes B. TGF-β1 mediated upregulation of VEGFxxxb was inhibited by the p38MAPK inhibitor SB203580. C. Reducing western blot of podocyte cell lysate showing that treatment with the p38MAPK inhibitor SB203580 inhibited the TGF- β1 mediated upregulation of VEGF$_{165}$b.

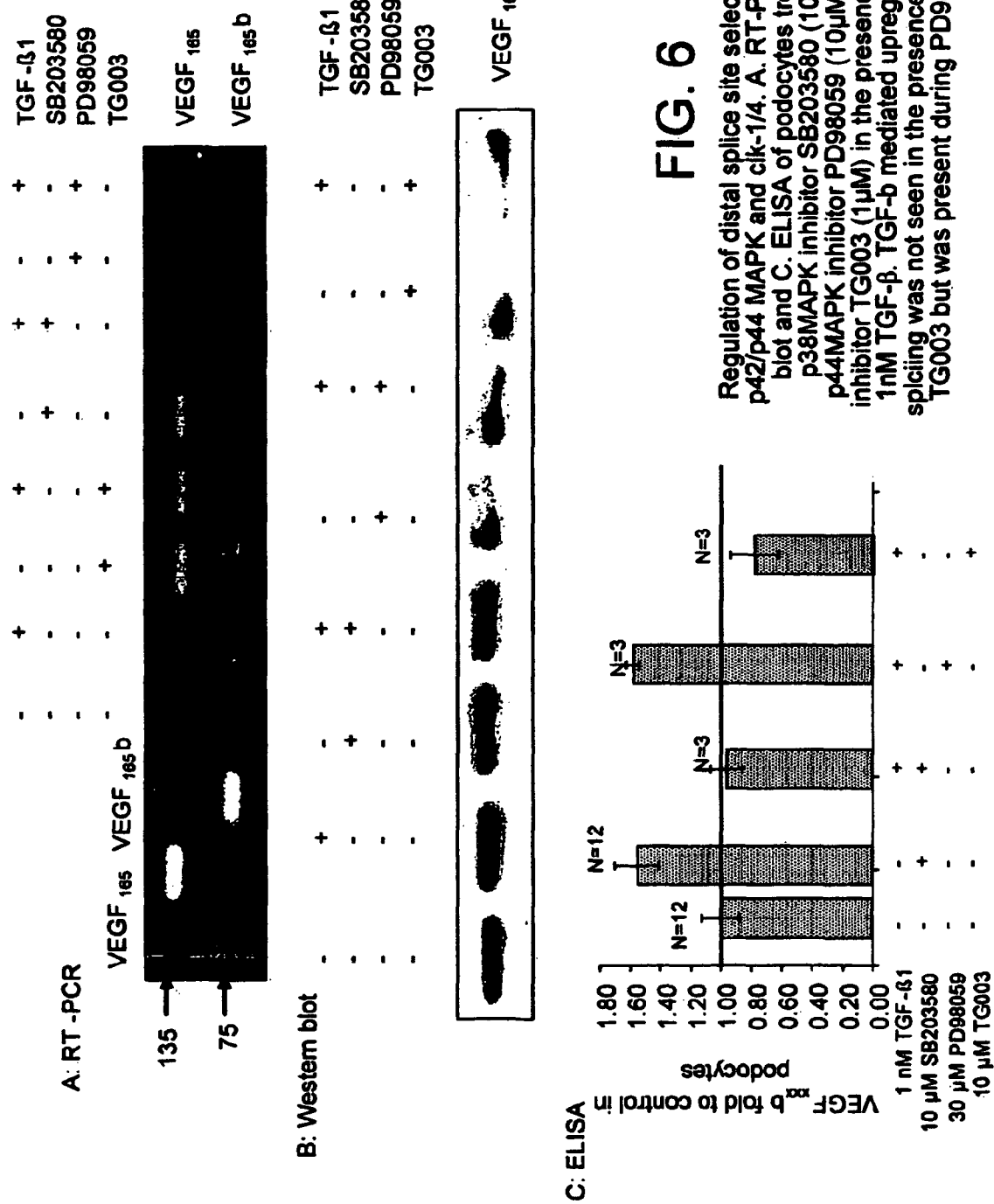

FIG. 6

Regulation of distal splice site selection by p38 and p42/p44 MAPK and clk-1/4. A. RT-PCR. B. Western blot and C. ELISA of podocytes treated with the p38MAPK inhibitor SB203580 (10µM), the p42/p44MAPK inhibitor PD98059 (10µM) or the Clk/Sty inhibitor TG003 (1µM) in the presence or absence of 1nM TGF-β. TGF-b mediated upregulation of distal splicing was not seen in the presence of SB203580 or TG003 but was present during PD98059 treatment.

Distribution of ESE consensus sequences in C terminus of VEGF gene.

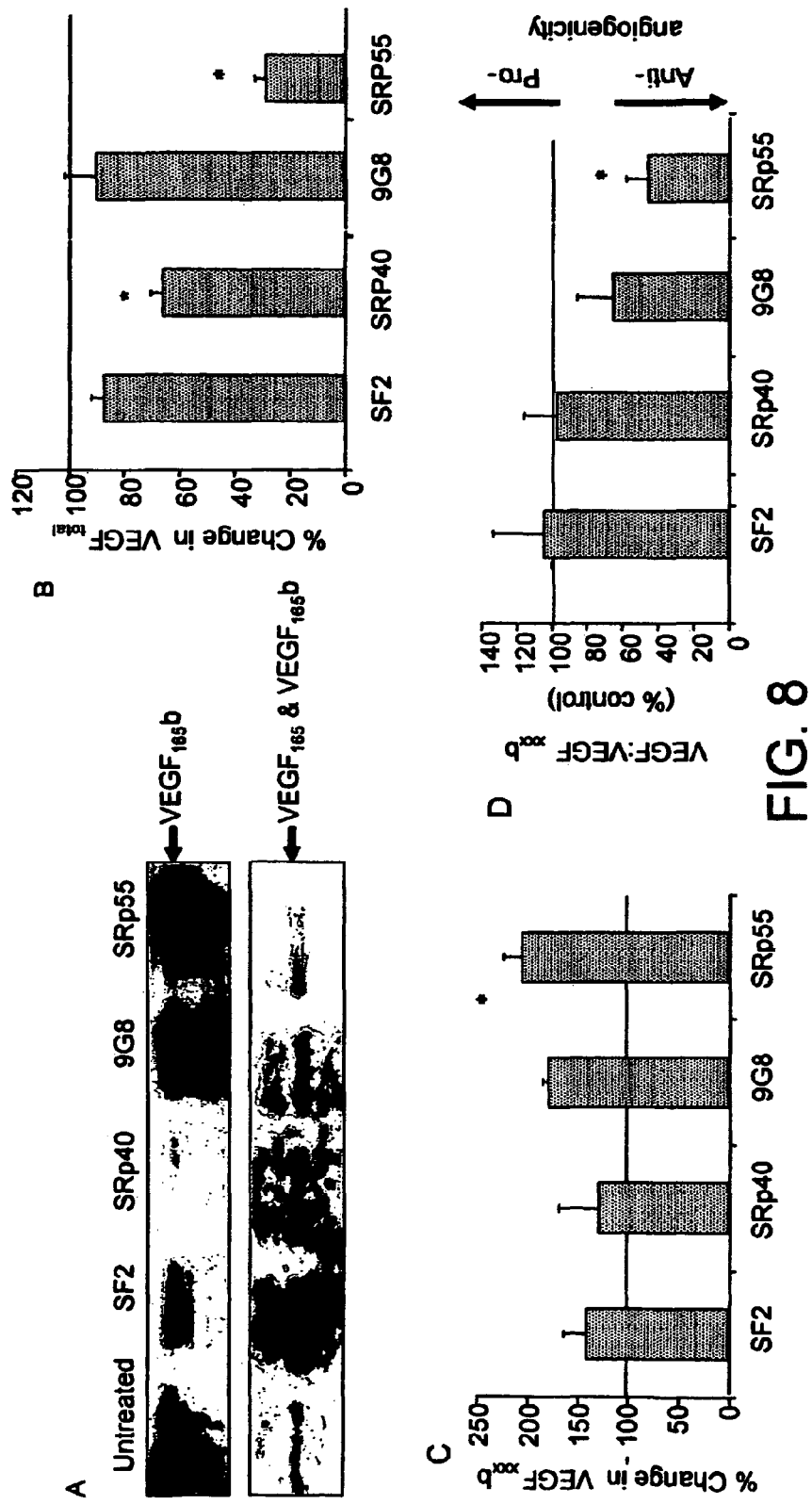

FIG. 8

Effect of over-expression of splicing factors on VEGF isoform production. Transfection of retinal pigmented epithelial cells with splicing factors differentially altered distal splicing isoforms and total VEGF levels. A. Western blot of cell lysates showing that VEGF165b expression was increased by SRp55, but decreased by SRp40, and was unchanged by SF2/ASF or 9G8. In contrast antibodies that detect both VEGF165 and VEGF165b (VEGFtotal) show an upregulation of SF2/ASF. B. ELISA of cell supernatant showed that trasnfection with SRp55 significantly reduced total VEGF levels. C. In contrast, SRp55 significantly increased VEGF165b production in the cell supernatant. D. the ratio of total VEGF to VEGFxxxb was significantly down regulated by SRp55 (*=p<0.05 comapred with control, ANOVA)

The balance between proximal and distal splicing is regulated by the expression of splicing factors. Over-expression of ASF/SF2 and SRp40 result in an increase in proximal splicing (increased $VEGF_{165}$ relative to $VEGF_{165}b$), whereas SRp55 over-expression induces distal splicing.

RT-PCR for SRPK1 and VEGF165b as cells undergo differentation in podocytes. The VEGF165b levels increase as the SRPK1 levels drop, consistent with a SRPK1 mediated switch from anti-angiogenic to proangigoenic isoforms.

Treatment of podocytes with IGF increases proximal splicing as evidenced by RT-PCR. This increase is inhibited by the PKC inhibitor BIM, and the SR protein kinase inhibitor SERPIN340.

Treatment of podocytes with IGF increases production of proteins encoded by proximal splicing as evidenced by ELISA. This increase is inhibited by the the PKC inhibitor BIM, and the SR protein kinase inhibitor SERPIN340. *p<0.05, **p<0.01 one-way ANOVA, Tukey's Test (ELISA)

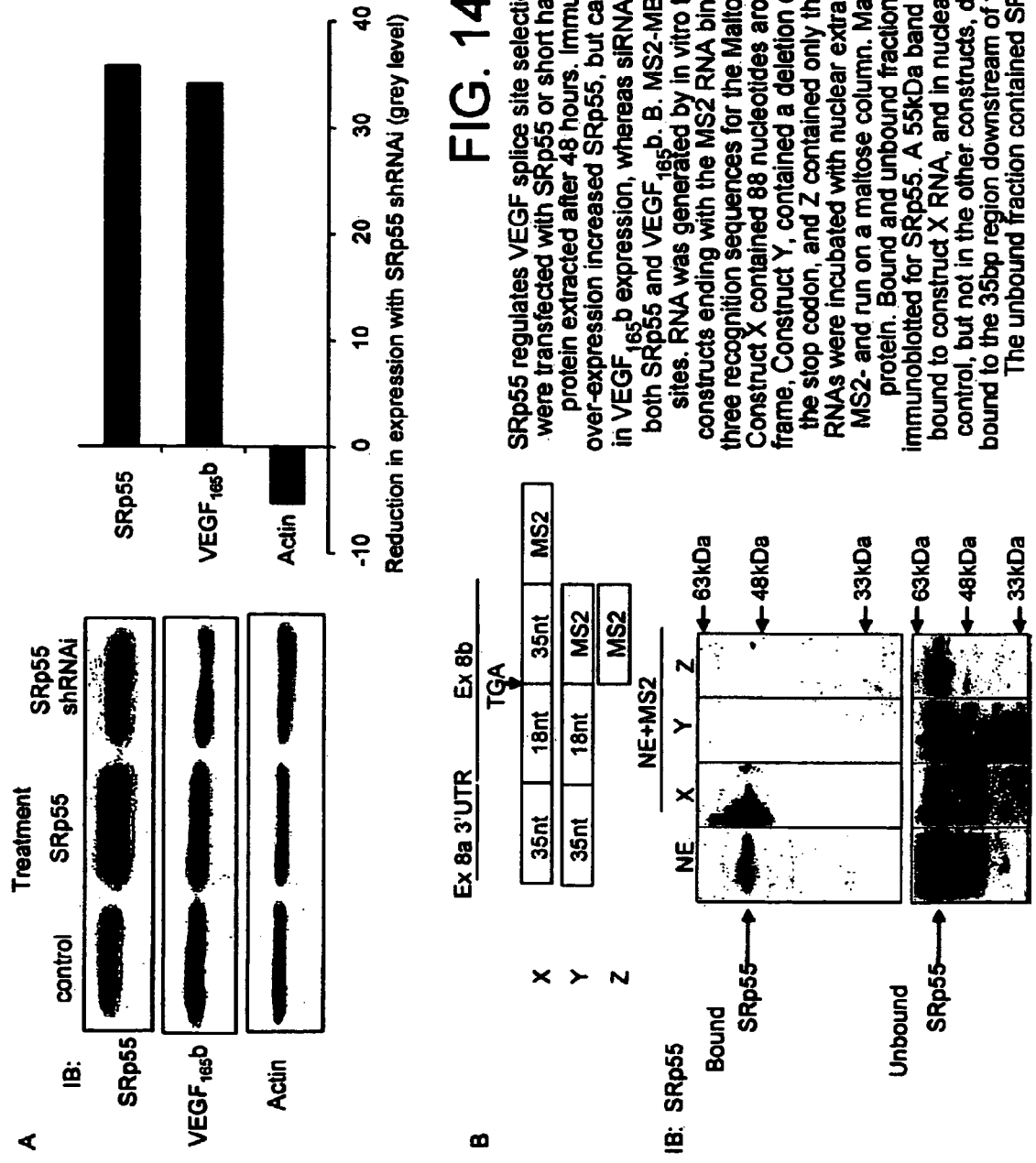

FIG. 14

SRp55 regulates VEGF splice site selection in exon 8. A. Podocytes were transfected with SRp55 or short hairpin RNA for SRp55 and protein extracted after 48 hours. Immunoblotting showed that over-expression increased SRp55, but caused a very slight increase in $VEGF_{165}b$ expression, whereas siRNA for SRp55 downregulated both SRp55 and $VEGF_{165}b$. B. MS2-MBP assay for RNA binding sites. RNA was generated by in vitro transcription from three constructs ending with the MS2 RNA binding sequence containing three recognition sequences for the Maltose Binding protein (MBP). Construct X contained 88 nucleotides around exon 8b open reading frame, Construct Y, contained a deletion of the 35bp downstream of the stop codon, and Z contained only the MS2 sequence. These RNAs were incubated with nuclear extract from HEK293 cells and MS2- and run on a maltose column. Maltose binds to MS2-MBP protein. Bound and unbound fractions were collected, and immunoblotted for SRp55. A 55kDa band was seen in the fractioned bound to construct X RNA, and in nuclear extract run as a positive control, but not in the other constructs, demonstrating that SRp55 bound to the 35bp region downstream of the stop codon in exon 8b. The unbound fraction contained SRp55 in all samples.

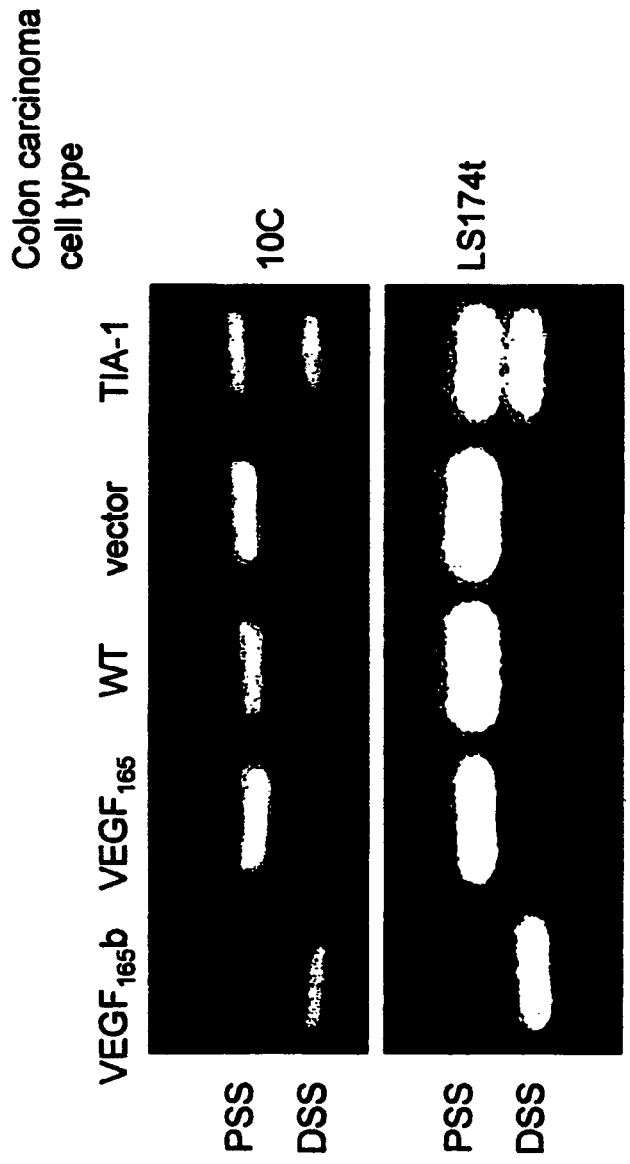

FIG. 15

TIA-1 (T-cell intercellular antigen-1) is a splicing regulator of VEGF. Colon carcinoma cells (10C and LS174t) that normally express less (10C) or little VEGF$_{165}$b were transfected with empty vector or TIA-1 cDNA. Tia-1 is an RNA-Binding protein previously shown by Maryam to be mutated in 10C cells. RNA was extracted and subjected to PCR using forward primers in exon 7 and reverse primers in the 3'UTR of the VEGF mRNA. The lower band is a result of distal splice site (DSS) selection (encoding VEGF$_{165}$b) and the upper band of the proximal splice site selection (VEGF$_{165}$). This indicates that TIA-1 activation may be a potential anti-angiogenic therapeutic strategy.

Morpholino treatment of HEK cells can dose dependently reduce the ratio of $VEGF_{165}b:VEGF_{165}$ (%). A. Sequence digram showing location of morpholino against distal splice site (MO-DSS). B. RT-PCR reaction showing effect of increasing concentration of MO-DSS. C. Quantification of ratio of $VEGF_{165}b:VEGF_{165}$ by densitometry.

Morpholino treatment of HEK cells can dose dependently increase the ratio of $VEGF_{165}b:VEGF_{165}$ (%). A. Sequence digram showing location of morpholino against proximal splice site (MO-PSS). B. RT-PCR reaction showing effect of increasing concentration of MO-PSS. C. Quantification of ratio of $VEGF_{165}b:VEGF_{165}$ by densitometry.

SEQUENCE LISTING

```
<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Cys Asp Lys Pro Arg Arg
1               5

<210> SEQ ID NO 2
<211> LENGTH: 6
<212> TYPE: PRT
<213> ORGANISM: Homo sapiens

<400> SEQUENCE: 2

Ser Leu Thr Arg Lys Asp
1               5

<210> SEQ ID NO 3
<211> LENGTH: 25
<212> TYPE: DNA
<213> ORGANISM: Artificial
<220> FEATURE:
<223> OTHER INFORMATION: Synthetic, morpholino
<220> FEATURE:
```

```
<221> NAME/KEY: modified_base
<222> LOCATION: (1)..(25)
<223> OTHER INFORMATION: These bases are morpholino bases and not
      conventional DNA or RNA bases

<400> SEQUENCE: 3
gtcacatctg agggaaatgg aaaac                                          25

<210> SEQ ID NO 4
<211> LENGTH: 24
<212> TYPE: DNA
<213> ORGANISM: Artificial
<220> FEATURE:
<223> OTHER INFORMATION: Synthetic, morpholino
<220> FEATURE:
<221> NAME/KEY: modified_base
<222> LOCATION: (1)..(24)
<223> OTHER INFORMATION: These bases are morpholino bases and are not
      conventional DNA or RNA bases

<400> SEQUENCE: 4
ggtgagagat ctggttcccg aaac                                           24
```

PRO- AND ANTI-ANGIOGENIC TREATMENTS

CROSS-REFERENCE TO RELATED APPLICATIONS

This is a national application of International Serial No. PCT/GB2008/000824, filed Mar. 10, 2008 which claims priority of British Patent Application No. 0704678.2, filed Mar. 9, 2007. The disclosures of the applications identified in this paragraph are incorporated herein by reference in their entireties.

FIELD OF THE INVENTION

The present invention relates to pro- and anti-angiogenic treatments and to compositions for use therein.

BACKGROUND OF THE INVENTION

The content of the publications referred to in the following discussion is in each case incorporated herein by reference in all respects relevant to the understanding and performance of the present invention.

Angiogenesis is a significant underlying pathological process in many, if not all, of the major human and other mammalian diseases of the western world. In addition to cancer, for example, it is a prominent feature of vascular disease (atheromatous plaque development requires proliferation of the vaso vasorum), diabetes, rheumatoid arthritis, proliferative retinopathy. The predominance of angiogenesis within clinical pathologies and the relatively limited role in normal physiology (in comparison to cell division) underpins the proposal that anti-angiogenic therapy may be an effective and generally well tolerated treatment modality, particularly but not exclusively in patients with life threatening disease.

VEGF pre-mRNA is differentially spliced from 8 exons to form mRNAs encoding at least six proteins (38) that have been widely studied and accepted as pro-angiogenic pro-permeability vasodilators. The most studied form has 165 amino acids in final structure and is termed $VEGF_{165}$. In 2002, an alternative isoform, $VEGF_{165}b$, was identified (2 and WO-A-03/012105), generated by differential splice acceptor site selection in the 3'UTR of exon 8 of the VEGF gene (see FIG. 1A of the accompanying drawings), thus resulting in two sub-exons, termed exon 8a (previously called exon 8) and exon 8b (previously called exon 9), in keeping with the nomenclature for exon 6 (24). Distal splicing into the splice acceptor site for exon 8b results in an open reading frame of 18 bases. The open reading frames of Exons 8a and 8b both code for 6 amino acids; exon 8a for Cys-Asp-Lys-Pro-Arg-Arg and exon 8b for Ser-Leu-Thr-Arg-Lys-Asp. This alternative splicing predicted an alternate family of VEGF isoforms (complementary to the existing isoforms) expressed as multiple proteins in human cells and tissues, of which $VEGF_{121}b$, $VEGF_{165}b$, $VEGF_{145}b$ and $VEGF_{189}b$ have now identified (42). The family has been termed $VEGF_{xxx}b$ where xxx is the amino acid number (see FIG. 1B of the accompanying drawings). This alternate C terminus enables $VEGF_{165}b$ to inhibit $VEGF_{165}$ induced endothelial proliferation, migration, vasodilatation (2), and in vivo angiogenesis and tumour growth (54). These effects were shown to be specific for VEGF, since $VEGF_{165}b$ does not affect fibroblast growth factor (FGF)-induced endothelial cell growth or proliferation. Moreover, unlike all other VEGF isoforms, $VEGF_{165}b$ is down-regulated in cancers so far investigated, including renal cell (2), prostate (54) and colon carcinoma (52) and malignant melanoma (44). Furthermore, VEGF splice variant expression is altered in angiogenic microvascular phenotypes of proliferative eye disease and pre-eclampsia (3, 42). The receptor binding domains are still present in $VEGF_{165}b$, and hence it acts as a competitive inhibitor of $VEGF_{165}$; it binds to the receptor but does not stimulate the full tyrosine phosphorylation of the VEGFR activated by $VEGF_{165}$ (4, 54). This isoform therefore appears to be an endogenous anti-angiogenic agent formed by differential splicing.

The nomenclature, described above, of the alternative splice variants of the C terminal exon 8 of the VEGF gene, which identifies as exon 8a the portion of exon 8 adjacent the proximal splice site and coding for the aminoacid sequence CDKPRR (SEQ. ID. No. 1) and as exon 8b the portion of exon 8 adjacent the distal splice site and coding for the amino-acid sequence SLTRKD (SEQ. ID. No. 2), will be used herein in place of the older nomenclature used, for example, in WO-A-03/012105 (see FIG. 4a of WO-A-03/012105, which Figure is hereby specifically incorporated herein by reference), which identified the exon coding for SEQ. ID. No. 1 as exon 8 and the exon coding for SEQ. ID. No. 2 as "exon 9".

Alternative splicing is a mechanism of differential gene expression that allows inclusion or substitution of specific exons and the production of structurally and functionally distinct proteins from a single coding sequence (27, 48). It is widely accepted that alternative splicing of VEGF that results in the conventional pro-angiogenic family is fundamental to the regulation of its bioavailability; the inclusion and exclusion of exons 6 and 7, which contain the heparin binding domains, affect the generation of diffusible proteins (24). Moreover, VEGF gene expression is transcriptionally regulated by a diversity of factors including hypoxia (47), growth factors and cytokines (18) (29) (40) (1), hormones (49, 8), oncogenes and tumour suppressor genes (45, 37). Despite the importance of the pro- and anti-angiogenic VEGF isoforms in regulating the angiogenic 'switch' in a wide variety of disease states, and in contrast to the well described regulation of mRNA VEGF transcription, almost nothing is known about the molecular and cellular pathways that regulate alternative splicing of VEGF in general and C'terminal splicing in particular. Of the more than 18,000 manuscripts published on VEGF, only three have investigated regulation of splicing, namely (30, 9, 12).

mRNA splicing occurs during transcription (36) mediated by splicing proteins which form the spliceosome (5). Splicing is regulated, however, by splicing regulatory factors (SRFs). These include the Serine/arginine Residue (SR) proteins (e.g. 9G8, SF2/ASF, Srp40, Srp55, etc) that regulate binding to exon splicing enhancers (ESEs) in the mRNA (5).

General mechanisms of splicing can be regulated genetically: base sequences in the transcript influence splice factor affinities (33), and promoters can also influence alternative splicing through the selective recruitment of splice factors to the C terminal domain of RNA polymerase 1 (23). It is also clear now that signal transduction pathways can influence alternative splicing in response to environmental cues (13, 26). A sequence mutation in tumours could theoretically result in altered splicing. However, as splicing from $VEGF_{165}$ to $VEGF_{165}b$ has previously been demonstrated upon differentiation of glomerular epithelial cells (11), this splicing is unlikely to be mutation-dependent.

Pre-mRNA has intronic and exonic sequences that bind SRFs—splicing enhancers and silencers (22). Exon splicing depends upon the balance of activities of SR proteins, including SF2/ASF, Srp40, Srp55, and 9G8. Furthermore growth factors such as Insulin-like Growth Factor-1 (IGF-1), Transforming Growth Factor-$\beta_1$ (TGF-$\beta_1$) and Platelet-derived Growth Factor (PDGF) have previously been shown to increase total VEGF expression, but their effect on terminal exon splice site selection was previously unknown (16, 18, 31, 34).

We have investigated the potential role of SR splicing factors, kinases, and growth factors in VEGF terminal exon splicing.

The present invention is based in one aspect on our surprising finding from this work, that agents which cause distal splice site (DSS) selection in exon 8 of VEGF to be favoured (see FIGS. 1 and 4a of WO-A-03/012105 and FIG. 1 of the accompanying drawings) can play an important role in regulating the alternative splicing in favour of the anti-angiogenic VEGF$_{xxx}$b isoforms, an effect which appears to be general to all the VEGF isoforms so far studied, from which we have established that VEGF-exon-8-DSS enhancers and/or VEGF-exon-8-PSS (proximal splice site) inhibitors and their in vivo activators, upregulators and potentiators, modified forms of any of the foregoing having a secondary functionality useful for control of their primary activity or the effects thereof, and expression vector systems for expressing any of the foregoing agents in vivo, will have valuable therapeutic activities in anti-angiogenic therapies.

The present invention is based in another aspect on our surprising finding from this work, that agents which cause PSS selection in exon 8 of VEGF to be favoured (see FIGS. 1 and 4a of WO-A-03/012105 and FIG. 1 of the accompanying drawings) can play an important role in regulating the alternative splicing in favour of the pro-angiogenic VEGF$_{xxx}$ isoforms, an effect which appears to be general to all the VEGF isoforms so far studied, from which we have established that VEGF-exon-8-PSS enhancers and/or VEGF-exon-8-DSS inhibitors and their in vivo activators, upregulators and potentiators, modified forms of any of the foregoing having a secondary functionality useful for control of their primary activity or the effects thereof, and expression vector systems for expressing any of the foregoing agents in vivo, will have valuable therapeutic activities in pro-angiogenic therapies.

DESCRIPTION OF THE INVENTION

Introduction

In a first aspect, the present invention provides a method of selectively pro- or anti-angiogenic treatment of a mammalian subject, particularly but not exclusively a human subject, the method comprising site-specific control of alternative splicing during processing of VEGF pre-mRNA transcribed from the C terminal exon 8 of the VEGF gene using controlling agents for the splicing, wherein one or more controlling agent which favours proximal splice site (PSS) splicing in said processing is used in the pro-angiogenic treatment and one or more controlling agent which favours distal splice site (DSS) splicing in said processing is used in the anti-angiogenic treatment.

The PSS splicing favours inclusion, in the C terminal domain of the expressed VEGF, of the amino acid sequence of SEQ. ID. No. 1 encoded by exon 8a of the VEGF gene, leading to expression of generally pro-angiogenic isoforms of VEGF.

The DSS splicing favours inclusion, in the C terminal domain of the expressed VEGF, of the amino acid sequence of SEQ. ID. No. 2 encoded by exon 8b of the VEGF gene, leading to expression of generally anti-angiogenic isoforms of VEGF.

The controlling agent which favours PSS splicing may if desired be used in association with one or more other controlling agents for the splicing which suppresses or inhibits DSS splicing.

The controlling agent which favours DSS splicing may if desired be used in association with one or more other controlling agents for the splicing which suppresses or inhibits PSS splicing.

The controlling agents used in the present invention may if desired be adjusted during the treatment period to switch between pro- and anti-angiogenic treatment. The switch may proceed either from pro- to anti- or from anti- to pro-, and may be performed once or repeated back and forth as desired during the treatment.

The control of the pro- and/or anti-angiogenic treatment, including control of switching between the two, may conveniently be exercised by way of co-agents or secondary agents present, which act on portions of the controlling agents or undergo controlling related processes or compete with the controlling agents and thereby control their activities and/or the splice site selectivity. Alternatively or additionally, the control of the pro- and/or anti-angiogenic treatment may be exercised by selecting the controlling agent for the process. The controlling agent may incorporate at least one activatable and deactivatable domain, for further control. Please see the discussion under "Agents" below for further information.

The pro-angiogenic treatment favours in particular the production of one or more of the VEGF isoforms VEGF$_{121}$, VEGF$_{145}$, VEGF$_{165}$, VEGF$_{183}$ and VEGF$_{189}$, particularly VEGF$_{165}$. The anti-angiogenic treatment favours in particular the production of one or more of the VEGF isoforms VEGF$_{121}$b, VEGF$_{145}$b, VEGF$_{165}$b, VEGF$_{183}$b and VEGF$_{189}$b, particularly VEGF$_{165}$b.

In one embodiment the treatment can be performed by administering to a subject in need of anti-angiogenic treatment an effective amount of one or more agent, by any conventional route of administration, selected from VEGF-exon-8-DSS enhancers and VEGF-exon-8-PSS inhibitors, their in vivo activators, upregulators and potentiators, modified forms of any of the foregoing having a secondary functionality useful for control of their primary activity or the effects thereof, and an expression vector system for expressing any of the foregoing agents in vivo, or any combination thereof. The administration route may, for example, be chosen from oral, intravenous (IV), intramuscular (IM), intraperitoneal (IP) and intra-arterial administration, administration into a cavity such as, for example, pleural space or bladder, and administration into the eye or into the cerebrospinal fluid (CSF).

In a second aspect, the present invention provides a VEGF-exon-8-DSS enhancer or a VEGF-exon-8-PSS inhibitor, or an in vivo activator, upregulator or potentiator thereof, modified forms of any of the foregoing having a secondary functionality useful for control of their primary activity or the effects thereof, or an expression vector system for expressing any of the foregoing agents in vivo, or any combination thereof, for use in a method of anti-angiogenic treatment of a mammalian subject, particularly but not exclusively a human subject.

In a third aspect, the present invention provides a composition, for example a medicament, for use in a method of anti-angiogenic treatment of a mammalian subject, particularly but not exclusively a human subject, the composition comprising an effective amount of a VEGF-exon-8-DSS enhancer or a VEGF-exon-8-PSS inhibitor, or an in vivo activator, upregulator or potentiator thereof, modified forms of any of the foregoing having a secondary functionality useful for control of their primary activity or the effects thereof, or an expression vector system for expressing any of the foregoing agents in vivo, or any combination thereof, in association or admixture with a physiologically acceptable carrier, diluent or excipient.

In a fourth aspect, the present invention provides the use of a VEGF-exon-8-DSS enhancer or a VEGF-exon-8-PSS inhibitor, or an in vivo activator, upregulator or potentiator thereof, modified forms of any of the foregoing having a secondary functionality useful for control of their primary activity or the effects thereof, or an expression vector system for expressing any of the foregoing agents in vivo, or any combination thereof, for use in the manufacture of a medicament for anti-angiogenic therapy in a mammalian subject, particularly but not exclusively a human subject.

Such agents as mentioned in connection with the second, third and fourth aspects of the present invention include, for example, Transforming Growth Factor (TGF)-β1, TGF-β R1, SRPK1 and/or SRPK2 specific inhibitors (for example, SRPIN 340, a specific inhibitor of SRPK1 and SRPK2 kinases), T-cell intercellular antigen-1 (TIA-1), MKK3/MKK6-activatable MAP kinases (for example, p38 MAPK), Cdc20-like (Clk) family kinases Clk1/sty, Clk2, Clk3 and Clk4, the SR splicing factor SRp55, their in vivo activators, upregulators and potentiators, functionally active analogues and functionally active fragments of any of the foregoing, modified forms of any of the foregoing having a secondary functionality useful for control of their primary activity or the effects thereof, expression vector systems for expressing any of the foregoing agents in vivo, transcription/translation blocking agents which bind to the PSS of exon 8a of the pre-mRNA and/or at the region of the pre-mRNA to which a splicing regulatory protein binds, to inhibit proximal splicing (for example, morpholinos or other synthetic blocking agents, peptide conjugates, RNA binding proteins, RNA interference (RNAi) poly- and oligonucleotide blocking agents (for example dsRNA, microRNA (miRNA), siRNA), peptide nucleic acid (PNA), protein kinase C (PKC) inhibitors (for example, bisindolyl maleimide (BIM) and other mechanistically analogous PKC inhibitors, particularly inhibitors which bind at the PKC catalytic domain), or any combination thereof. All of such materials, including the expression vector systems, are referred to herein as "agents". For further details, please see the section below headed "Agents".

The anti-angiogenic treatment preferably includes the treatment or prevention of any disease or disorder associated with abnormal angiogenesis or abnormal over-production of pro-angiogenic VEGF isoforms (VEGF$_{xxx}$). Such diseases and disorders include, for example, vascular disease (e.g. vasoconstriction and disorders characterised by vasoconstriction, and cardiovascular disease), malignant and benign neoplasia (e.g. angiogenesis-dependent cancers, for example tumorous cancers), tumor metastasis, inflammatory disorders, diabetes, diabetic retinopathy and other complications of diabetes (e.g. diabetic neovascularisation), trachoma, retrolental hyperplasia, neovascular glaucoma, age-related macular degeneration, haemangioma, immune rejection of implanted corneal tissue, corneal angiogenesis associated with ocular injury or infection, Osler-Webber Syndrome, myocardial angiogenesis, wound granulation, telangiectasia, hemophiliac joints, angiofibroma, telangiectasia psoriasis scleroderma, pyogenic granuloma, coronary collaterals, ischemic limb angiogenesis, rubeosis, obesity, arthritis (e.g. rheumatoid arthritis), hematopoieses, vasculogenesis, gingivitis, atherosclerosis, endometriosis, neointimal hyperplasia, psoriasis, hirsutism and proliferative retinopathy. The anti-angiogenic treatment according to the present invention may also include non-therapeutic treatments performed on healthy subjects, for example to inhibit vascular development for cosmetic purposes.

In another embodiment of the first aspect of the present invention, the treatment can be performed by administering to a subject in need of pro-angiogenic treatment an effective amount of one or more agent selected from VEGF-exon-8-PSS enhancers and VEGF-exon-8-DSS inhibitors, their in vivo activators, upregulators and potentiators, modified forms of any of the foregoing having a secondary functionality useful for control of their primary activity or the effects thereof, and an expression vector system for expressing any of the foregoing agents in vivo, or any combination thereof.

In a fifth aspect, the present invention provides a VEGF-exon-8-PSS enhancer or a VEGF-exon-8-DSS inhibitor, or an in vivo activator, upregulator or potentiator thereof, a modified form of any of the foregoing having a secondary functionality useful for control of its primary activity or the effects thereof, or an expression vector system for expressing any of the foregoing agents in vivo, or any combination thereof, for use in a method of pro-angiogenic treatment of in a mammalian subject, particularly but not exclusively a human subject.

In a sixth aspect, the present invention provides a composition, for example a medicament, for use in a method of pro-angiogenic treatment of a mammalian subject, particularly but not exclusively a human subject, the composition comprising an effective amount of a VEGF-exon-8-PSS enhancer or a VEGF-exon-8-DSS inhibitor, or an in vivo activator, upregulator or potentiator thereof, a modified form of any of the foregoing having a secondary functionality useful for control of its primary activity or the effects thereof, or an expression vector system for expressing any of the foregoing agents in vivo, or any combination thereof, in association or admixture with a physiologically acceptable carrier, diluent or excipient.

In a seventh aspect, the present invention provides the use of a VEGF-exon-8-PSS enhancer or a VEGF-exon-8-DSS inhibitor, or an in vivo activator, upregulator or potentiator thereof, modified forms of any of the foregoing having a secondary functionality useful for control of their primary activity or the effects thereof, or an expression vector system for expressing any of the foregoing agents in vivo, or any combination thereof, for use in the manufacture of a medicament for pro-angiogenic therapy in an mammalian subject, particularly but not exclusively a human subject.

Such agents as mentioned in connection with the fifth, sixth and seventh aspects of the present invention include, for example, Insulin-like Growth Factor-1 (IGF-1), IGF-R, Tumor Necrosis Factor (TNF)-α, Alternative Splicing Factor/Splicing Factor 2 (ASF/SF2), Srp40, their in vivo activators, upregulators and potentiators, functionally active analogues and functionally active fragments of any of the foregoing, modified forms of any of the foregoing having a secondary functionality useful for control of their primary activity or the effects thereof, expression vector systems for expressing any of the foregoing agents in vivo, transcription/translation blocking agents which bind to the DSS of exon 8a of the pre-mRNA and/or at the region of the pre-mRNA to which a splicing regulatory protein binds, to inhibit distal splicing (for example, morpholinos or other synthetic blocking agents, peptide conjugates, RNA binding proteins, RNA interference (RNAi) poly- and oligonucleotide blocking agents (for example dsRNA, microRNA (miRNA), siRNA), peptide nucleic acid (PNA), or any combination thereof. Specific inhibitors of the agents leading preferentially to DSS, such as TG003 and SB203580, may also serve as agents as mentioned in connection with the fifth, sixth and seventh aspects of the present invention. All of such materials, including the expression vector systems, are referred to herein as "agents". For further details, please see the section below headed "Agents".

The pro-angiogenic treatment preferably includes the treatment or prevention of any disease or disorder associated with abnormally reduced angiogenesis or abnormal underproduction of pro-angiogenic VEGF isoforms (VEGF$_{xxx}$). Such diseases and disorders include, for example, preeclampsia, myocardial infarction, vascular injury, coronary artery disease, peripheral vascular disease, ischaemia (including solid organ ischaemia), ischaemic attacks, angina, cerebrovascular injury (for example, stroke, head injury). The pro-angiogenic treatment can also serve to assist revascularisation, for example in wound healing following injury, including metabolic injury (for example diabetes) and peripheral pressure injury (for example bed sores) or surgery, for example following tissue transplantation or prosthetic implantation, or in tissue culture methods (e.g. culture of skin sheets for use in surgery, or construction of scaffold-supported tissue prostheses for implantation). The pro-angiogenic treatment can also serve therapeutically or non-therapeutically to support aspects of mammalian, for example human or farm animal, reproduction, for example ovulation, fertility, implantation, endometrial and ovarian function and lactation. In one example of non-therapeutic use of the present invention for supporting aspects of mammalian reproduction, control of ovulation, fertility and lactation in connection with animal husbandry and farming is mentioned. The pro-angiogenic treatment according to the present invention can also be used non-therapeutically in humans, for example to improve endurance or athletic performance, for example in athletics and sports, or to promote vascularisation for cosmetic purposes.

In an eighth aspect, the present invention provides a method of facilitating the diagnosis or prognosis in a mammalian subject, particularly but not exclusively a human subject, of a condition or disorder associated with angiogenesis, the method comprising obtaining a sample of body tissue or fluid from the patient and testing the sample to determine the relative presence and absence, or potential relative presence or absence, in the sample of controlling agents favouring PSS splicing during processing of VEGF pre-mRNA transcribed from the C terminal exon 8 of the VEGF gene and controlling agents favouring DSS splicing during processing of VEGF pre-mRNA transcribed from the C terminal exon 8 of the VEGF gene. The said determination of the controlling agents in the sample may be qualitative or quantitative.

The controlling agents detected in the sample may be any of the agents defined and described as VEGF-exon-8-DSS enhancers or inhibitors or as VEGF-exon-8-PSS enhancers or inhibitors, including their in vivo activators, upregulators or potentiators, or modified forms of any of the foregoing having a secondary functionality useful for control of their primary activity or the effects thereof. The potential relative presence or absence or the controlling agents in the sample may, for example, be detected by analysis of gene mutations in the subject which may influence the extent of expression of the naturally occurring agents in the subject, as opposed to the expression of mutated (less active or inactive) forms of the agents.

The sample of body tissue or fluid may, for example, be selected from hair, skin, invasively obtained biopsy tissue, non-invasively obtained biopsy tissue, stool, milk, blood, blood serum, saliva, cerebrospinal fluid, mucus (e.g. smear sample from a mucosal membrane such as the mouth wall, tongue or cervix), sputum, urine or tears.

The testing of the sample may be carried out using any suitable assay system specific for the agent being detected. Suitable assay systems include immunoassays, for example sandwich immunoassays or competition immunoassays, for example ELISA, and there may be mentioned particularly immunoassays using monoclonal antibodies specific for the target agent to be detected. The immunoassays will typically use a detectable label selected from radioisotopes, enzymes, fluorochromes, chemiluminescent labels and labels detectable through electrical conductivity. Alternatively, or additionally, the agent being detected may be assayed using real time polymerase chain reaction (RT-PCR), including quantitative RT-PCR (qRT-PCR), and/or Western Blotting, as illustrated in more detail in the specific experiments described below.

Following the method according to the eighth aspect of the present invention, the data may if desired be used to assess the relative pro- and anti-angiogenic tendencies of the patient's biochemistry, from which the likelihood of development, relapse, progression or spread of the condition or disorder may be assessed.

The method according to the eighth aspect of the present invention may, for example, be used to facilitate the diagnosis or prognosis of any of the conditions previously mentioned in connection with any one or more of the first to seventh aspects of the invention. There may particularly be mentioned in this connection diagnosis or prognosis in relation to pregnancy, wound healing, pre-eclampsia, cancers (e.g. tumorous cancers), metastatic spread of cancers, failure of ovulation, lactation, visual loss and joint destruction.

The method according to the eighth aspect of the present invention may be followed by a treatment program designed, on the basis of the diagnosis or prognosis, for treating the patient's condition. During the said treatment program, the method according to the eighth aspect of the present invention may be repeated as desired, to monitor the progress of the treatment and/or to allow the diagnosis or prognosis to be updated. The treatment program may, for example, comprise the administration of conventional anti-angiogenic agents to the subject, or application of any one or more of the first to the seventh aspects of the present invention, or any combination thereof.

In the method according to the eighth aspect of the present invention, the diagnosis or prognosis to be facilitated may, for example, take into account a current or possible future treatment of the subject with an anti-angiogenic pharmaceutical, particularly a VEGF-blocker. If the method according to the eighth aspect of the present invention targets the sample for the presence or absence, or potential presence or absence, of one or more specific naturally occurring agents selected from (a) controlling agents favouring PSS splicing during processing of VEGF pre-mRNA transcribed from the C terminal exon 8 of the VEGF gene and (b) controlling agents favouring DSS splicing during processing of VEGF pre-mRNA transcribed from the C terminal exon 8 of the VEGF gene, and the result of the method is that the subject is shown to have a high level of agents of type (a), a high level of agents of type (b), a relatively high level of one or more agents of type (a) over type (b), a relatively high level of one or more agents of type (b) over type (a), or the potential to have this, then the effectiveness of a current or possible future treatment of the subject with an anti-angiogenic pharmaceutical, particularly a VEGF-blocker, may be predicted.

For example, naturally occurring VEGF-exon-8-DSS enhancers or VEGF-exon-8-PSS inhibitors, if predominating in a subject or tissue over naturally occurring VEGF-exon-8-PSS enhancers or VEGF-exon-8-DSS inhibitors, will lead to a predisposition of the subject towards expression of (anti-angiogenic) $VEGF_{xxx}b$. Such subjects will then be relatively resistant towards treatment of conditions associated with angiogenesis using anti-angiogenic VEGF-blockers. Such VEGF-blockers include, for example, humanised anti-VEGF antibodies (for example, bevacizumab (Avastin®)), used to treat certain cancers such as breast cancer, colon carcinoma and rectal carcinoma.

Naturally occurring VEGF-exon-8-PSS enhancers or VEGF-exon-8-DSS inhibitors, if predominating in a subject or tissue over naturally occurring VEGF-exon-8-DSS enhancers or VEGF-exon-8-PSS inhibitors, will lead to a predisposition of the subject towards expression of (pro-angiogenic) $VEGF_{xxx}$. Such subjects will then be relatively susceptible to treatment of conditions associated with angiogenesis using anti-angiogenic VEGF-blockers. Such VEGF-blockers include, for example, humanised anti-VEGF antibodies (for example, bevacizumab (Avastin®)), used to treat certain cancers such as breast cancer, colon carcinoma and rectal carcinoma.

Subjects carrying genes for one or more naturally occurring VEGF-exon-8-DSS enhancer or VEGF-exon-8-PSS inhibitor, for example selected from TGF-β1, TGF-β R1, SRPIN 340, TIA-1, p38 MAPK, Clk1/sty, Clk2, Clk3, Clk4, SRp55 and their naturally occurring activators, upregulators and potentiators, in whom expression of the normal protein takes place leading to the tendency to favour expression of $VEGF_{xxx}b$, will thus be expected to be relatively resistant to treatment for cancers and other diseases and conditions associated with aniogenesis using VEGF-blockers such as, for example, humanised anti-VEGF antibodies. Such a prediction may be reinforced if investigations of gene mutations in the subject indicate an impaired ability to express one or more naturally occurring VEGF-exon-8-PSS enhancer or VEGF-exon-8-DSS inhibitor.

On the other hand, subjects carrying mutated genes for one or more naturally occurring VEGF-exon-8-DSS enhancer or VEGF-exon-8-PSS inhibitor, for example selected from TGF-β1, TGF-β R1, SRPIN 340, TIA-1, p38 MAPK, Clk1/sty, Clk2, Clk3, Clk4, SRp55 and their naturally occurring activators, upregulators and potentiators, in whom expression of a less active or inactive variant form of the protein takes place leading to the tendency to favour expression of $VEGF_{xxx}$, will thus be expected to be relatively susceptible to treatment for cancers and other diseases and conditions associated with aniogenesis using VEGF-blockers such as, for example, humanised anti-VEGF antibodies. Such a prediction may be reinforced if gene investigations in the subjects indicate a normal ability to express one or more naturally occurring VEGF-exon-8-PSS enhancer or VEGF-exon-8-DSS inhibitor.

Testing for possible mutations of genes encoding one or more specific naturally occurring agents selected from (a) controlling agents favouring PSS splicing during processing of VEGF pre-mRNA transcribed from the C terminal exon 8 of the VEGF gene and (b) controlling agents favouring DSS splicing during processing of VEGF pre-mRNA transcribed from the C terminal exon 8 of the VEGF gene, may be carried out using conventional genotyping methods such as RT-PCR, in situ DNA hybridisation or such like. The genotyping is suitably carried out on the excised biopsy or tumor sample taken from the patient, or on other tissue or body fluid sample from the patient.

In one particularly mentioned embodiment, the present invention is used to facilitate prognosis of a cancer in a patient, for example selected from breast cancer, colon carcinoma and rectal carcinoma, taking into account a current or possible future treatment of the subject with a VEGF-blocker such as, for example bevacizumab, by investigating the presence or absence of genetic mutations of the subject in relation to one or more naturally occurring VEGF-exon-8-DSS enhancer or VEGF-exon-8-PSS inhibitor, for example selected from TGF-β1, TGF-β R1, SRPIN 340, TIA-1, p38 MAPK, Clk1/sty, Clk2, Clk3, Clk4, SRp55 and their naturally occurring activators, upregulators and potentiators, preferably TIA-1, to determine the likely susceptibility or resistance of the subject to the said treatment from the presence or absence of genetic mutations of the subject in relation to the said one or more naturally occurring VEGF-exon-8-DSS enhancer or VEGF-exon-8-PSS inhibitor. Such a method thus has the potential to avoid wasted health service resources and to avoid ineffective treatment of patients who are not able to respond fully or at all to such treatments.

The present invention also provides a rationale for the development of diagnostic agents and methods in relation to the susceptibility of a potential lesion or condition to a pro- or anti-angiogenic therapeutic strategy. It has been observed that the anti- to pro-angiogenic switch is heterogeneous in patients with the same clinical condition, e.g. diabetic retinopathy (42) and colonic carcinoma (52). Detailed analysis of the balance of $VEGF_{xxx}/VEGF_{xxx}b$ isoform expression may thus predict susceptibility of the individual patient's lesion or condition to treatment, or to a particular treatment, or allow the specific tailoring of treatment for the individual patient, increasing therapeutic effectiveness and reducing side effects or the particular result of side effects or therapies for that patient (bearing in mind particular intolerances, allergies or contraindications in relation to that patient).

The details, examples and preferences provided above in relation to any particular one or more of the stated aspects of the present invention, and described and exemplified below in relation to any particular one or more of the stated aspects of the present invention, apply equally to all aspects of the present invention.

For avoidance of doubt, it is hereby stated that the controlling agents used in the present invention favour/suppress, as desired, PSS or DSS in the processing of VEGF pre-mRNA transcribed from the C terminal exon 8 of the VEGF gene. From this it is implicit that the terms "VEGF-exon-8-PSS enhancers", "VEGF-exon-8-DSS enhancers", "VEGF-exon-8-PSS inhibitors" and "VEGF-exon-8-DSS inhibitors" used herein refer to agents which act directly on the processing (post-transcriptional modification) of the VEGF pre-mRNA, transcribed from the C terminal exon 8 of the VEGF gene, in the nucleus before the mature, alternatively-spliced, mRNA is exported to the cytoplasm. As is well know, such post-transcriptional modification in the nucleus typically includes removal of transcribed introns and reconnection of the exons according to the control mechanism(s) in operation for the alternative splicing. Such control mechanism(s) in the present invention are believed to include direct action on nuclear splicing regulatory proteins and the mRNA material undergoing processing in the nucleus.

From this it follows that controlling agents which act solely on mature mRNA outside of the nucleus are not considered to be "controlling agents for the splicing", "VEGF-exon-8-PSS enhancers", "VEGF-exon-8-DSS enhancers", "VEGF-exon-8-PSS inhibitors" and "VEGF-exon-8-DSS inhibitors" as those terms are used in connection with the present invention.

Agents

Functionally active analogues and functionally active fragments of agents which are splicing factors may include, for example, the protein binding domain or the RNA binding domain or both of these domains. Such analogues or fragments may, if desired, be conjugated to one or more other active molecule, for example an up- or down-regulator of splicing or a molecule which directs splicing one way or the other as between DSS and PSS. Such molecules may include, for example, other splicing factors or RNA degrading molecules.

Functionally active analogues and functionally active fragments of agents which are splicing factors may further include, for example, the phosphorylation target domain by which the protein can be activated or deactivated. This can allow a further degree of control of the agent in operation of the present invention. The phosphorylation target domain can, for example, be blocked, permanently or reversibly, by a specific binding partner for the domain, to temporarily or permanently prevent activation, or a secondary compound which contains the phosphorylation target domain can be present, for example in excess, to compete with the primary agent for phosphorylation and thus effectively restrict activation of the primary agent.

Functionally active analogues and functionally active fragments of agents which are kinases may include, for example, the kinase regulatory domain or the active domain or both domains. Such analogues or fragments may, if desired, be conjugated to one or more other active molecule, for example an up- or down-regulator of splicing or a molecule which directs splicing one way or the other as between DSS and PSS. Such molecules may include, for example, other splicing factors or RNA degrading molecules.

Coagents or secondary agents for enabling the desired functionality or combination of functionalities of the agents used in the present invention may be present as required in conjunction with the primary agents, as will be well understood by those skilled in this art.

Transcription/translation blocking agents which bind to the DSS or PSS of exon 8a of the pre-mRNA and/or at the region of the pre-mRNA to which a splicing regulatory protein binds, to inhibit respectively distal or proximal splicing, include, for example, morpholinos or other synthetic blocking agents, peptide conjugates, RNA binding proteins, RNA interference (RNAi) poly- and oligonucleotide blocking agents (for example dsRNA, microRNA (miRNA), siRNA), peptide nucleic acid (PNA).

A suitable morpholino for blocking the PSS of exon 8a will be a 22- to 27-base phophorodiamidate morpholino oligo having a base sequence complementary to a sequence of bases spanning the 5' end of exon 8a. The base sequence of the morpholino may, for example, be 3'-CAAAAGG-TAAAGGGAGTCTACACTG-5' (SEQ. ID. NO. 3) or have sufficient homology with such a sequence to hybridise to the VEGF gene at the exon 8a PSS, for example at least about 85%, e.g. at least about 90%, homology with the sequence.

A suitable morpholino for blocking the DSS of exon 8a will be a 22- to 27-base phophorodiamidate morpholino oligo having a base sequence complementary to a sequence of bases spanning the 3' end of exon 8a. The base sequence of such a morpholino may, for example, be 3'-CAAAGCCCT-TGGTCTAGAGAGTGG-5' (SEQ. ID. NO. 4) or have sufficient homology with such a sequence to hybridise to the VEGF gene at the exon 8a DSS, for example at least about 85%, e.g. at least about 90%, homology with the sequence.

The term "morpholino" used herein is intended to refer generally to the class of synthetic blocking analogues of nucleotides which provide steric blocking by hybridisation to portions of the pre-mRNA sequence but are non-replicating systems. While the phophorodiamidate morpholino oligo system provides a well-known example of a class of such blocking agents, the expression "morpholino" is not to be understood as limited to this class, and extends to analogous non-replicating blocking agents in which a synthetic molecular backbone provides a foundation to a base sequence which can hybridise to the VEGF pre-mRNA at the DSS or PSS to cause regulation of the alternative splicing mechanism in accordance with the present invention.

A suitable nucleotide blocking agent which can hybridise to the VEGF pre-mRNA at the DSS or PSS to cause regulation of the alternative splicing mechanism in accordance with the present invention may, for example, be siRNA.

The illustration in FIG. 10C of the accompanying drawings, and the legend to that figure and its discussion below, summarises the controlling pathway by which the selection of DSS splicing or PSS splicing may be achieved and controlled according to the present invention. Inhibitors of the controlling agents, including for example SRPIN340, SB203580 and TG003 as shown, can be used for additional control of the activation and direction of the splicing during processing of the VEGF pre-mRNA. Clk/Sty favours distal splicing and inhibits proximal splicing. A pathway TGF-β1 leading to TGF-β R1 leading to p38MAPK leading to Clk/Sty leading to distal splicing via SRp55 has been identified. A pathway IGF-1 leading to IGF-R leading to SRPK1 leading to proximal splicing via ASF/SF2 has been identified. SRPIN340 inhibits SPRK1. TG003 inhibits Clk/Sty. SB203580 specifically inhibits p38MAPK. As shown in FIG. 6 and the accompanying discussion below, TGF-β1 induced $VEGF_{xxx}b$ expression was not affected by inhibition of p42/44 MAP kinase phosphorylation by PD98059, and TG003, an inhibitor of the Clk family of kinases implicated in splicing control by phosphorylating splicing factors, inhibited TGF-β1 induced $VEGF_{xxx}b$ expression. These results indicate that TGF-β1 stimulates the synthesis of $VEGF_{xxx}b$ isoforms through p38 MAPK and Clk kinases.

The non-vector agents for use in the present invention, including functional fragments and analogues thereof can suitably be obtained by transfection of a suitable host cell to introduce into its genome exogenous DNA and suitable promoters and optionally other control sequences, culturing the cells in a suitable growth medium and harvesting of the expressed protein, in conventional manner. Examples of such a method are provided below. The nucleotide and amino acid sequences of the non-vector agents are generally known, and the organisation and functionality of the various molecule domains is sufficiently well established that the selection of agents for the purposes of this invention is not burdensome following the teachings we make here. Testing of harvested expressed molecules for activity is simply conducted in the manner shown in the following examples.

The vector agents are prepared as recombinant viruses containing in their genome exogenous DNA and suitable promoters and optionally other control sequences, again starting from the published nucleotide and amino acid sequences in generally known manner. Further details are provided below in the section headed "Gene Therapy".

Compositions and Administration

The active agent according to the present invention may be administered in the form of a composition comprising the active agent and any suitable additional component. The composition may, for example, be a pharmaceutical composition (medicament), suitably for parenteral administration (e.g. injection, implantation or infusion). The composition may alternatively, for example, be a foodstuff, food supplement, beverage or beverage supplement.

The term "pharmaceutical composition" or "medicament" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally may be found in Remington, The Science and Practice of Pharmacy, Mack Publishing Co., Easton, Pa., latest edition.

Liquid form preparations include solutions, suspensions, and emulsions. As an example may be mentioned water or water-propylene glycol solutions for parenteral injection. Liquid preparations can also be formulated in solution in aqueous polyethylene glycol solution.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

The terms "foodstuff", "food supplement", "beverage" and "beverage supplement" used herein have the normal meanings for those terms, and are not restricted to pharmaceutical preparations. Other composition forms are also included within the present invention. These may, for example, include pure or substantially pure compound as such, a foodstuff precursor such as a rehydratable powder or a beverage precursor such as a powder dispersible in water, milk or other liquid.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

Gene Therapy

The present invention may alternatively be practiced using gene therapy. Gene therapy techniques are generally known in this art, and the present invention may suitably be put into practice in these generally known ways. The following discussion provides further outline explanation.

The gene therapies are broadly classified into two categories, i.e., in vivo and in vitro therapies. The in vivo gene therapy comprises introducing a therapeutic gene directly into the body, and the in vitro gene therapy comprises culturing a target cell in vitro, introducing a gene into the cell, and then, introducing the genetically modified cell into the body.

The gene transfer technologies are broadly divided into a viral vector-based transfer method using virus as a carrier, a non-viral delivery method using synthetic phospholipid or synthetic cationic polymer, and a physical method, such as electroporation or introducing a gene by applying temporary electrical stimulation to a cell membrane.

Among the gene transfer technologies, the viral vector-based transfer method is considered to be preferable for the gene therapy because the transfer of a genetic factor can be efficiently made with a vector with the loss of a portion or whole of replicative ability, which has a gene substituted a therapeutic gene. Examples of virus used as the virus carrier or vector include RNA virus vectors (retrovirus vectors, lentivirus vector, etc.), and DNA virus vectors (adenovirus vectors, adeno-associated virus vectors, etc.). In addition, its examples include herpes simplex viral vectors, alpha viral vectors, etc. Among them, retrovirus and adenovirus vectors are particularly actively studied.

The characteristics of retrovirus acting to integrate into the genome of host cells are that it is harmless to the human body, but can inhibit the function of normal cells upon integration. Also, it infects various cells, proliferates fast, can receive about 1-7 kb of foreign genes, and is capable of producing replication-deficient virus. However, it has disadvantages in that it is hard to infect cells after mitosis, it is difficult to transfer a gene in vivo, and the somatic cell tissue is needed to proliferate always in vitro. In addition, since it can be integrated into a proto-oncogene, it has the risk of mutation and can cause cell necrosis.

Meanwhile, adenovirus has various advantages for use as a cloning vector; it has moderate size, can be replicated within a cell nucleus, and is clinically nontoxic. Also, it is stable even when inserted with a foreign gene, and does not cause the rearrangement or loss of genes, can transform eukaryotes, and is stably expressed at a high level even when it is integrated into the chromosome of host cells. Good host cells for adenovirus are cells of causing human hematosis, lymphoma and myeloma. However, these cells are difficult to proliferate because they are linear DNAs. Also, it is not easy infected virus to be recovered, and they have low virus infection rate. Also, the expression of a transferred gene is the highest after 1-2 weeks, and in some cells, the expression is kept only for about 3-4 weeks. In addition, these have the problem of high immune antigenicity.

Adeno-associated virus (AAV) can overcome the above-described problems and at the same time, has many advantages for use as a gene therapeutic agent and thus is recently considered to be preferable. AAV, which is single-strand provirus, requires an assistant virus for replication, and the AAV genome is 4,680 bp in size and can be inserted into any site of chromosome 19 of infected cells. A trans-gene is inserted into plasmid DNA linked with 145 bp of each of two inverted terminal repeat sequence (ITR) and a signal sequence. This gene is transfected with another plasmid DNA expressing AAV rep and cap genes, and adenovirus is added as an assistant virus. AAV has advantages in that the range of its host cells to be transferred with a gene is wide, immune side effects due to repeated administration are little, and the gene expression time is long. Furthermore, it is stable even when the AAV genome is integrated into the chromosome of a host cell, and it does not cause the modification or rearrangement of gene expression in host cells. Since an AAV vector containing a CFTR gene was approved by NIH for the treatment of cystic fibrosis in 1994, it has been used for the clinical treatment of various diseases. An AAV vector containing a factor IX gene, which is a blood coagulation factor, is used for the treatment of hemophilia B, and the development of a therapeutic agent for hemophilia A with the AAV vector is currently being conducted. Also, AAV vectors containing various kinds of anticancer genes were certified for use as tumor vaccines.

Gene therapy, which is a method of treating diseases by gene transfer and expression, is used to adjust a certain gene, unlike the drug therapy. The ultimate purpose of the gene therapy is to obtain useful therapeutic effects by genetically modifying a living gene. The gene therapy has various advantages, such as the accurate transfer of a genetic factor into a disease site, the complete decomposition of the genetic factor in vivo, the absence of toxicity and immune antigenicity, and the long-term stable expression of the genetic factor and thus is spotlighted in connection with the present invention as a potentially suitable route of treatment.

BRIEF DESCRIPTION OF THE DRAWINGS

Embodiments of the present invention will now be described, purely by way of example, and with reference to the accompanying drawings, in which:

FIG. 5 shows the effect of p38-MAPK on the distal splice site selection in the VEGF terminal exon in podocytes, by an ELISA assay of the podocyte cell lysate for $VEGF_{xxx}b$ after treatment with the p38-MAPK inhibitor SB203580 (A) without and (B) with upregulation of the $VEGF_{xxx}b$ isoform using TGF-β1; and (C) reducing Western Blots of the lysates, details given in the legend and the discussion below;

FIG. 6 shows regulation of distal splice site selection by p38-MAPK and p42/p44-MAPK and clk-1/4 in podocytes, by (A) RT-PCR, (B) Western Blot and (C) an ELISA assay, details given in the legend and the discussion below;

FIG. 8 shows the effect of over-expression of certain splicing factors on the production of the VEGF isoforms in RPE cells, by (A) Western Blot of the cell lysates, and by ELISA assay of the cell lysates (supernatants) measuring for each splicing factor (B) the change in total VEGF isoforms produced, (C) the change in the b isoforms produced, and (D) the ratio of total VEGF to $VEGF_{xxx}b$ compared with control, details given in the legend and the discussion below;

FIG. 14 shows the effect of SRp55 transfection of podocytes, and siRNA targeting SRp55, on the regulation of VEGF splice site selection in exon 8, details given in the legend and the discussion below;

FIG. 15 shows the effect of TIA-1 transfection of colon carcinoma cells on $VEGF_{165}b$ mRNA, details given in the legend and the discussion below;

EXAMPLES AND DETAILED DESCRIPTION OF THE DRAWINGS

In the following discussion, the Examples are not numbered. The general materials and methods are first described, after which the results shown in the Figures are discussed and explained.

The legends included in the Figures form part of the following discussion and are to be referred to when reading the discussion. Their content is incorporated herein.

Introduction

Figure 1:
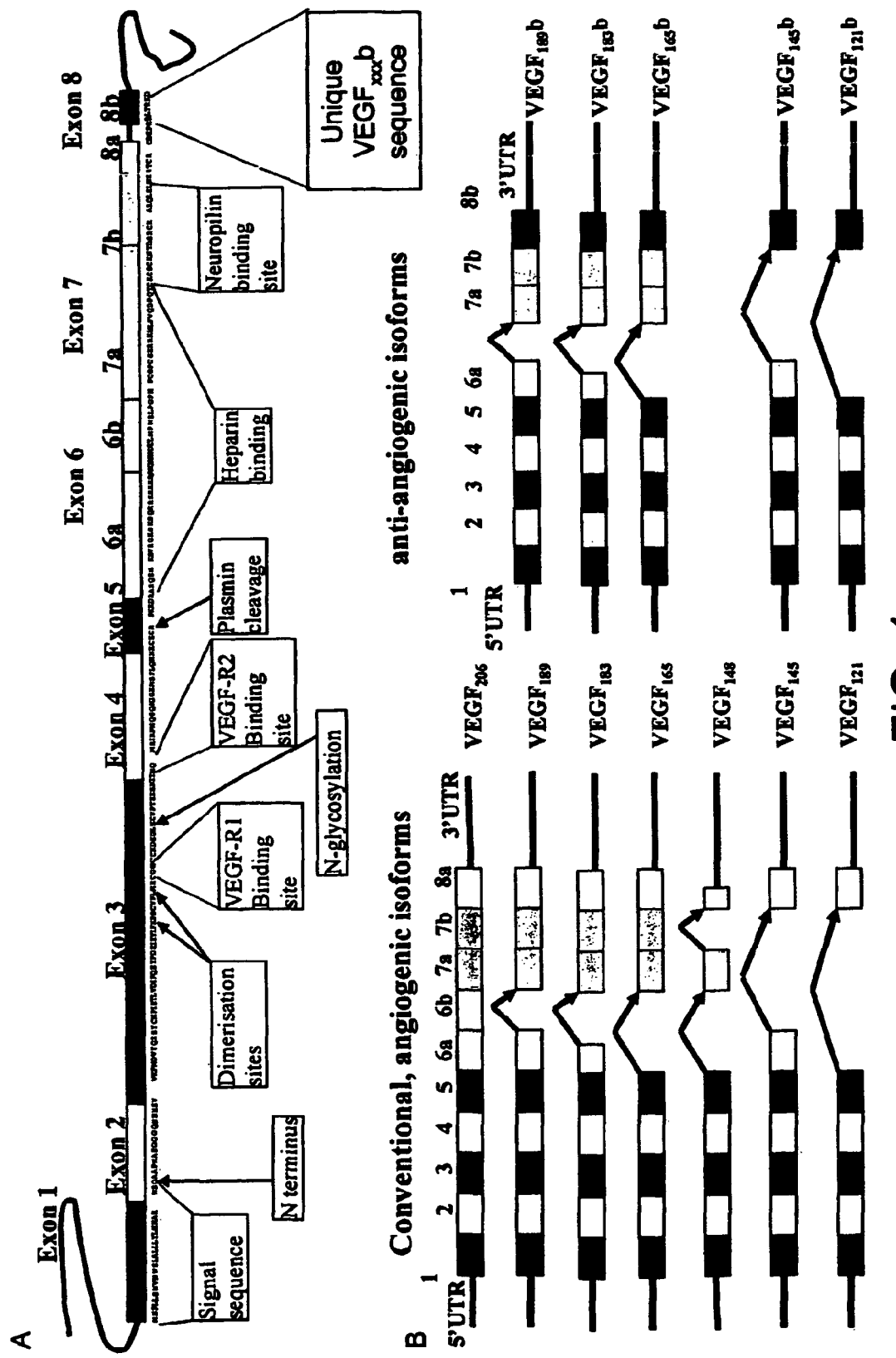
FIG. 1 shows (A) an exon map of the human VEGF gene, and (B) the exon splicing patterns that lead to different VEGF isoforms.

Despite the fact that 12 splice variants of VEGF have so far been identified (FIG. 1), with varying bioavailablity and activity, very few studies have considered the mechanisms of mRNA splicing of VEGF.

This is the first work to examine the effect of known splicing factors and other agents on C' terminal VEGF splicing, a process that may profoundly influence the angiogenic phenotype of a tissue.

Materials

The investigations used human retinal pigmented epithelial cells (RPE cells) and human Proliferating Conditionally Immortalized Podocytes (PCIP), as these cells are known to constitutively produce both $VEGF_{xxx}$ and $VEGF_{xxx}b$ isoforms (11).

The response of these cells to known splicing factors (SRp40, ASF/SF2, SRp55 & 9G8) and other environmental stimuli (IGF-1, TGF-β1 & PDGF) was tested, to investigate the hypothesis that these agents and stimuli could affect the relative (differential) expression of the $VEGF_{xxx}$ and $VEGF_{xxx}b$ isoform families.

The investigations to which FIG. 15 relates used 10C and LS174t human colon carcinoma cells. These cells normally express relatively low levels of $VEGF_{165}b$ isoform.

Figure 16:
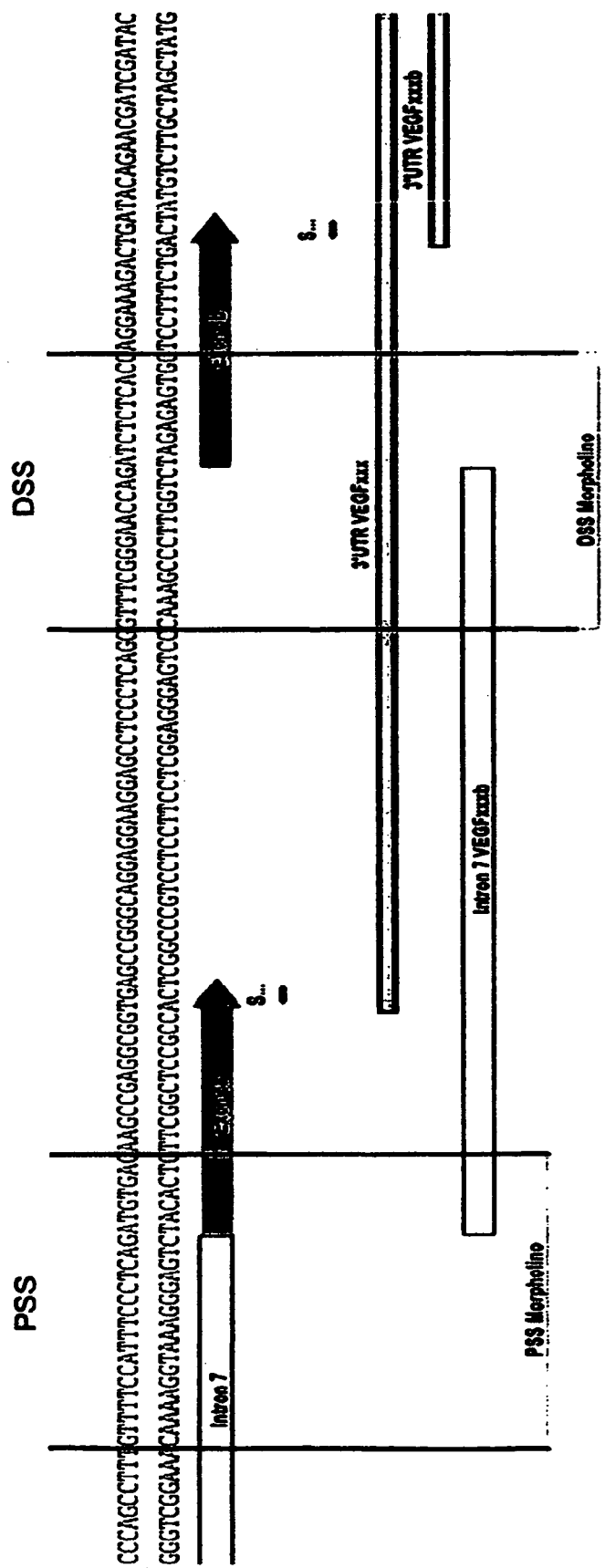
FIG. 16 shows the portions of exons 8a and 8b targeted by PSS and DSS morpholinos, details given in the legend and the discussion below.
Figure 17:
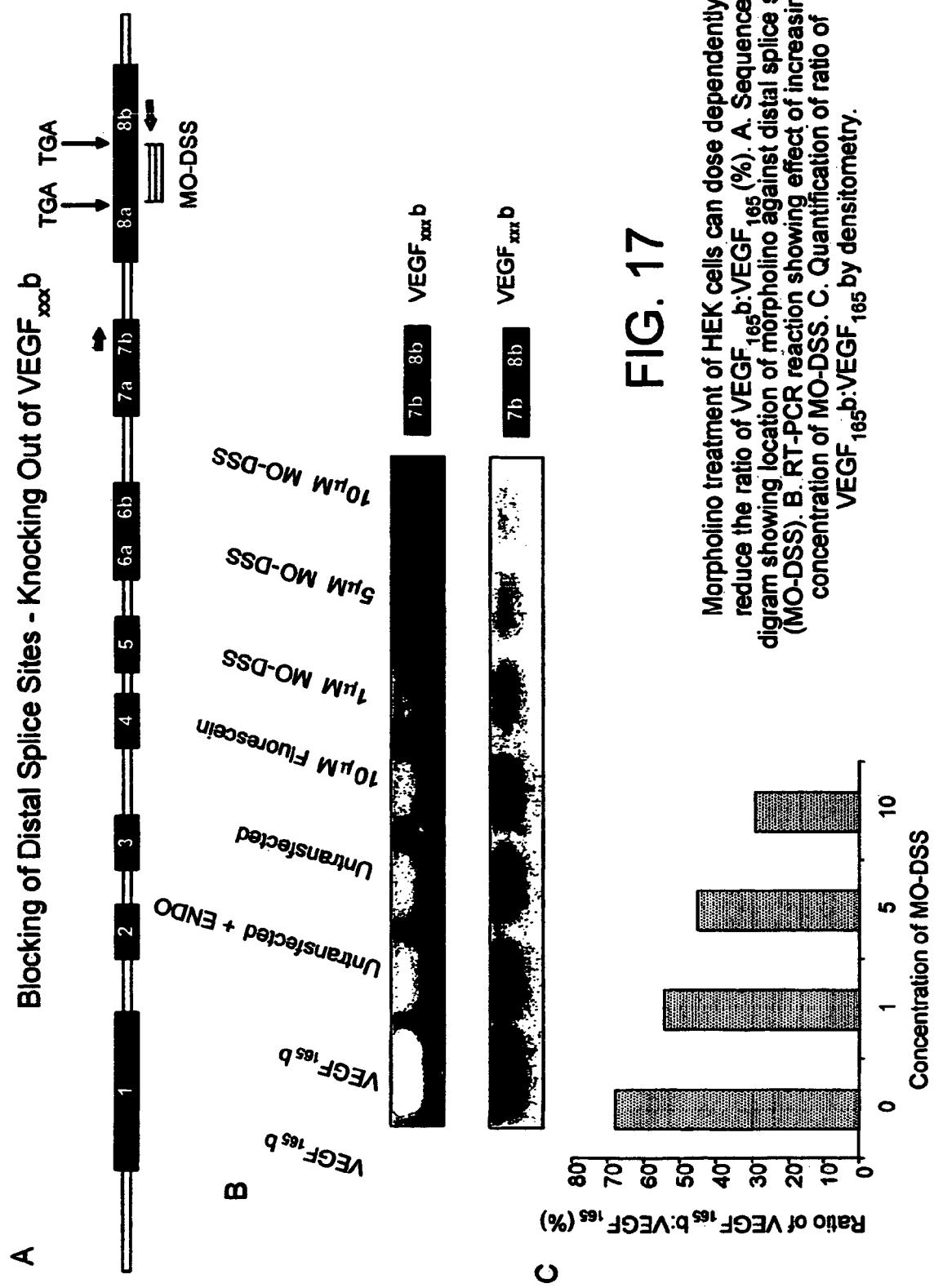
FIG. 17 shows the effect of DSS-targeting morpholino treatment of human embryonic kidney (HEK) cells on the expression of $VEGF_{165}b$, (a) the sequence diagram showing the location of the morpholino action, (b) the results of the morpholino action studied using RT-PCR, and (c) the quantification of the results of (b) in terms of the ratio of $VEGF_{165}b$ to $VEGF_{165}$, details given in the legend and the discussion below.
Figure 18:
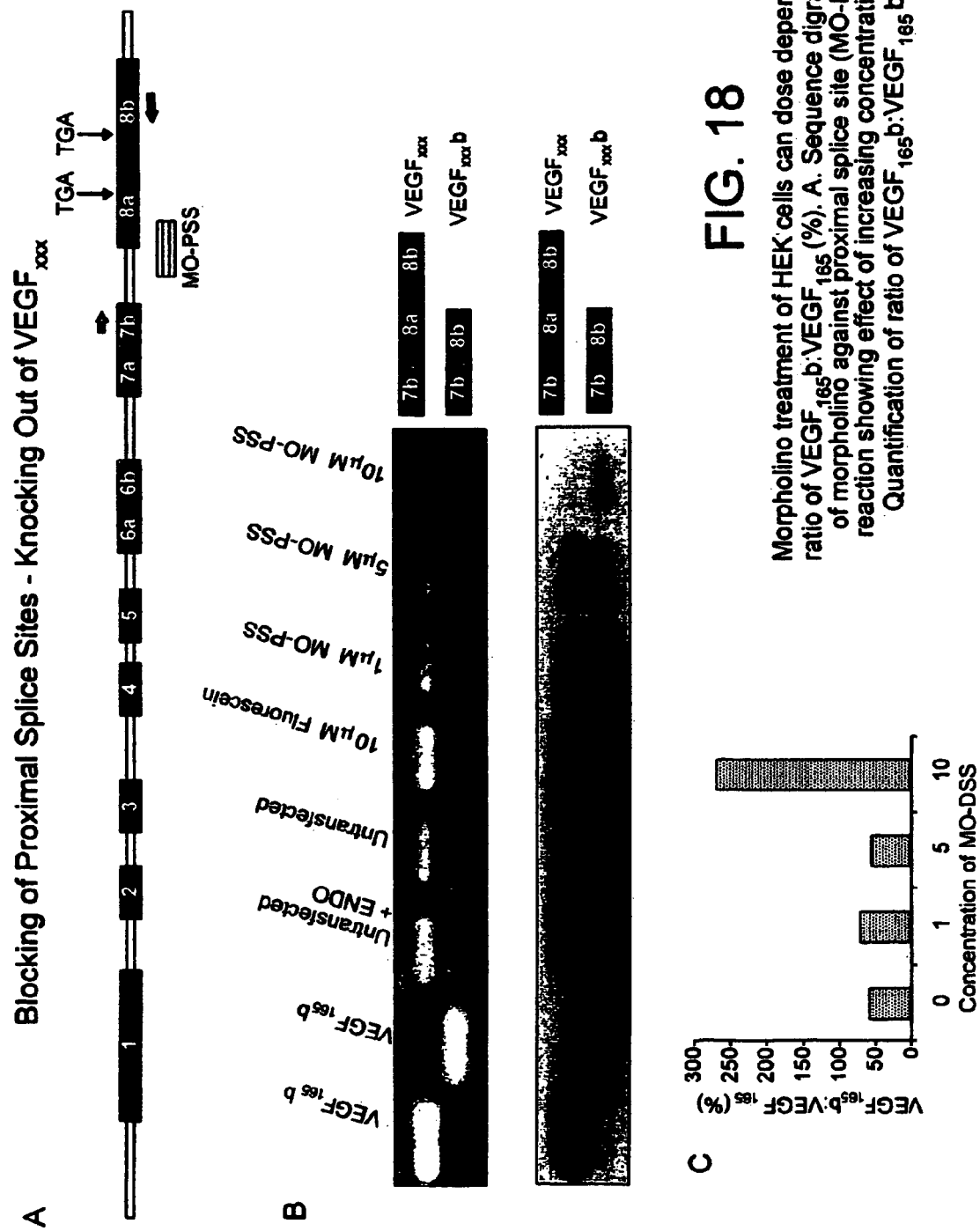
FIG. 18 shows the effect of PSS-targeting morpholino treatment of HEK cells on the expression of $VEGF_{165}b$, (a) the sequence diagram showing the location of the morpholino action, (b) the results of the morpholino action studied using RT-PCR, and (c) the quantification of the results of (b) in terms of the ratio of $VEGF_{165}b$ to $VEGF_{165}$, details given in the legend and the discussion below.

The investigations to which FIGS. 16 to 18 relate used HEK cells.

Figure 19:
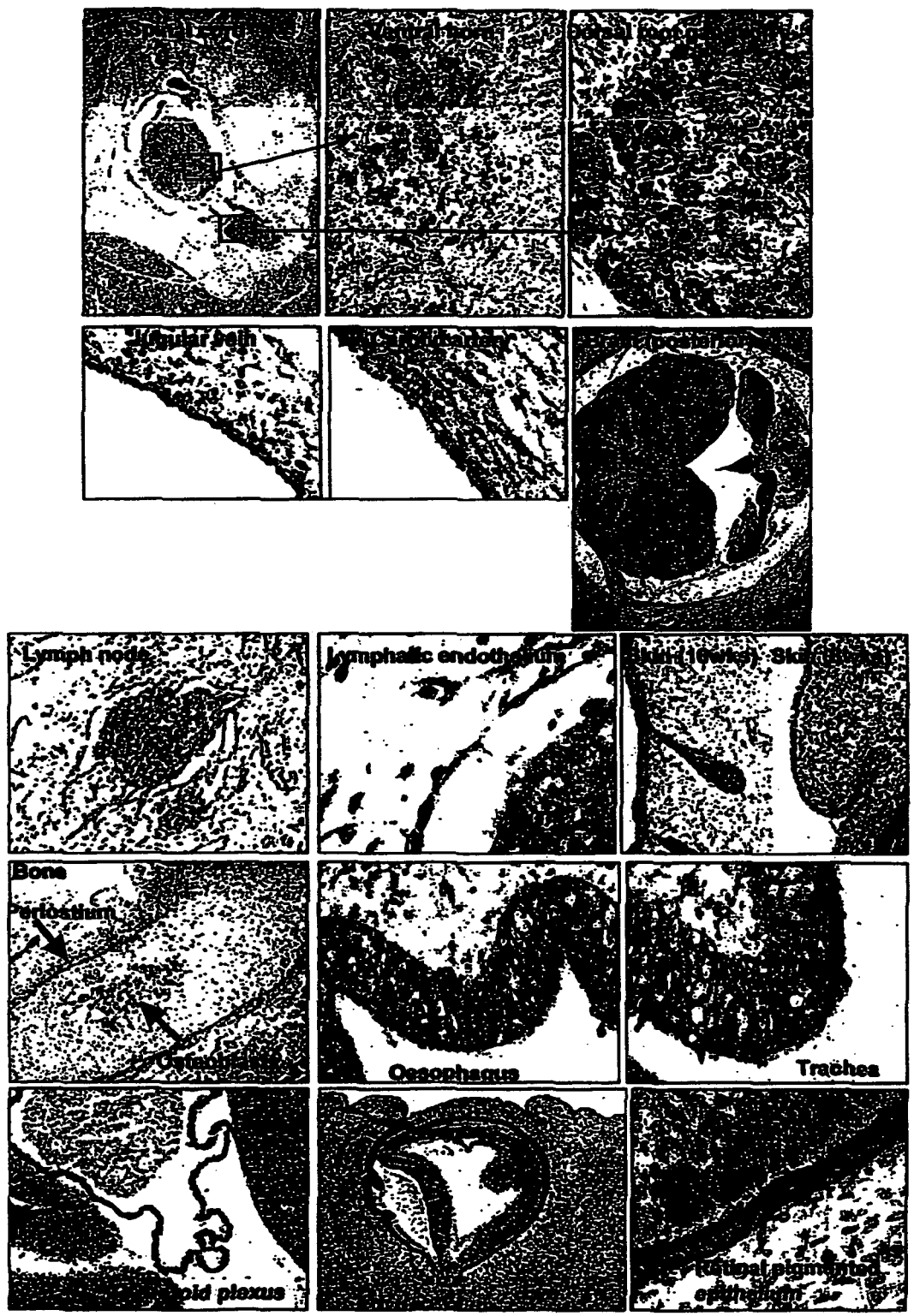
FIG. 19 shows photomicrographs from a study of the development of $VEGF_{xxx}b$ isoforms in a variety of tissues of human embryos.

The investigations to which FIG. 19 relates used the following tissues from 14 week human embryos (8 weeks and 16 weeks in the case of skin), as shown in the Figure (reading top to bottom, starting with the top left corner photograph and reading left to right along each line): spinal cord, ventral horn, dorsal root ganglion, jugular vein, carotid artery, brain (posterior), lymph node, lymphatic endothelium, skin, bone (periosteum and osteoblasts indicated by arrows), oesophagus, trachea, choroid plexus, eye and retinal pigmented epithelium.

Methods

Retinal Pigmented Epithelial (RPE) Cell Culture

Preparation

Human donor eyes were obtained within 10-30 hours post-mortem from Bristol Eye Bank, Bristol, United Kingdom. Choroid-RPE sheets dissected from ocular globes were fragmented in a small amount of Dulbecco's Modification of Eagle's Medium: Ham's F12 mixture (DMEM: F12) (1:1)+ GlutaMAX® supplement (Gibco) and RPE cells were isolated by digestion with 0.3 mg/ml collagenase (Gibco) for 15 min at 37° C. RPE cells were initially cultured for 5 days in the presence of 2.5% v/v foetal bovine serum (FBS) (Gibco) to prevent proliferation of fibroblasts and until the cell cultures became established. After the first passage cell culture was maintained in DMEM:F12 (1:1), supplemented with 10% v/v FBS and antibiotic/antimycotic solution (Sigma). The once passaged cells were homogeneous and contained only RPE as characterized by immunhistochemistry with anti-cytokeratin monoclonal antibody (Sigma). Cultures of RPE were routinely subcultured by trypsinisation (trypsin/EDTA, Sigma). RPE cells at passage 3-4 were plated onto 12.5 $cm^2$ Petri dishes (Nunc) and allowed to reach 70-80% confluency.

Tests

To determine the effects of agonists the RPE cells were cultured in freshly-replaced medium in the absence of FBS for 24 hours prior to agonist stimulation. IGF-1 (Sigma) and TNF-α (Sigma) were prepared in serum-free medium and were added in the volume of 2 ml at various concentrations, as indicated in the discussion below. No changes in cell morphology were noted on visualisation of the cells after stimulation. 24 hours later conditioned media in all experimental treatments were collected, spun down to remove debris, and placed immediately into −80° C. until the enzyme-linked immuno-sorbent assay (ELISA) was performed. The RPE cells were washed 3 times with ice-cold PBS and lysed in Laemmli buffer for Western blotting.

Podocyte Cell Culture

Preparation

Proliferating Conditionally Immortalized Podocytes (PCIPs) were derived from cell lines conditionally transformed from normal human podocytes with temperature-sensitive mutant of immortalized SV-40 (Simian Virus 40) T-antigen. At the permissive temperature of 33° C. the SV-40 T-antigen is active and allows the cells to proliferate rapidly (46). PCIPs were cultured in T75 flasks (Greiner) in RPMI-1640® cell culture medium (Sigma) with 10% FBS (Foetal Bovine Serum), 1% ITS (Insulin Transferrin Selenium) (Sigma), 0.5% PSS (Penicillin Streptomycin Solution) (Sigma) and grown to 95% confluency. Then cells were split to six well plates ($1 \times 10^4$ cells per well) and grown until 95% confluent.

Tests

We investigated time- and dose-dependent effects of Insulin-like Growth Factor 1 (IGF-1), Transforming Growth Factor β1 (TGF-β1) and Platelet-Derived Growth Factor (PDGF) on production of VEGF isoforms from cultured PCIPs. Twenty-four hours before treatment cultured medium was replaced with serum free RPMI-1654 medium (Sigma) containing 1% ITS (Sigma) and 0.5% PSS (Sigma). Subsequently, the medium was replaced with fresh serum free RPMI-1654 medium (Sigma) containing 1% ITS (Sigma), 0.5% PSS (Sigma) and increasing concentrations of IGF-1 (Sigma), or TGF-β1 (Sigma) or 40 ng/mL PDGF (Sigma). The conditioned media were collected 24 or 48 hours after stimulation (IGF-1, TGF-$β_1$) and 48 hours (PDGF).

Assessment of Protein Production following Transfection of Candidate Splicing Factors RPE cells were grown in six-well plates, each seeded with $3 \times 10^5$ cells and subsequently transfected using the expression vectors $pcDNA_3$-SRp40, $pcDNA_3$-ASF/SF2, $pcDNA_3$-SRp55, $pcDNA_3$-9G8 or the empty expression vector, $pcDNA_3$, using Lipofectamine (Invitrogen). Following incubation at 37° C. for 48 h, conditioned medium was collected and cells were lysed in buffer containing: 20 mM Tris, pH7.4, 1.5% w/v Triton X-100, 150 mM NaCl, 10% w/v glycerol and protease inhibitors cocktail (Sigma). VEGF isoforms were measured in cell lysate or conditioned media was measured using ELISA and protein production assessed via Western blotting, as described below.

Conditioned Media VEGF Measurements

Total VEGF concentrations in the neat RPE conditioned medium were measured using a standard DuoSet VEGF ELISA (R&D) according to manufacture's instruction. VEGF$_{xxx}$b was determined with a similar sandwich ELISA, using for capture a monoclonal biotinylated mouse anti-human antibody raised against the terminal nine amino acids of VEGF$_{165}$b (R&D Systems Cat No. MVRL56/1) and a standard curve for this assay built with recombinant human VEGF$_{165}$b (R&D). This MVRL56/1 antibody is a commercially available affinity purified mouse monoclonal IgG$_1$ antibody, that has been characterised previously (42, 54). It binds recombinant VEGF$_{165}$b, and shows expression of VEGF$_{165}$b, VEGF$_{189}$b, VEGF$_{121}$b VEGF$_{183}$b and VEGF$_{145}$b collectively termed VEGF$_{xxx}$b, but not VEGF$_{165}$. Western blotting has previously shown that all the proteins recognised by this antibody are also recognised by commercial antibodies raised against VEGF$_{165}$, conclusively demonstrating that this antibody is specific for VEGF$_{xxx}$b (54).

Due to relatively low levels of VEGF$_{xxx}$b found free in the supernatant of RPE cells, for VEGF$_{xxx}$b ELISA total protein in conditioned medium was precipitated with trichloroacetic acid (TCA). For this purpose 250 μl ice cold 24% TCA and 6.25 μl 2% Sodium Deoxycholate were added to 700 μl conditioned medium and left on ice for 15 min. After centrifugation at 5000×g for 10 min, pellets were collected and resuspended in lysis buffer, containing: 20 mM Tris, pH7.4, 1.5% w/v Triton X-100, 150 mM NaCl, 10% w/v glycerol and protease inhibitors cocktail (Sigma). The pH in the pelleted samples was adjusted to 7.4 with 1.5M Tris (pH8.8). The total protein content in the pellet was measured in conventional manner using bicinchoninic acid (BCA) reagent (Sigma).

Western Blotting

Protein samples were dissolved in Laemmli buffer, boiled for 3-4 min and centrifuged for 2 min at 20,000 g to remove insoluble materials. 15 μg protein per lane were separated by Sodium Dodecyl Sulfate Polyacrylamide Gel Electrophoresis (SDS/PAGE) (12%) and transferred to 0.2 μm nitrocellulose membrane. The blocked membranes were probed overnight (4° C.) with antibodies against panVEGF (R&D; MAB 293, 1:500), VEGF$_{xxx}$b (in house clone 56/1; 1:250) and β-tubulin (Sigma; 1:2000). Subsequently the membranes were incubated with secondary horseradish peroxidase (HRP) conjugated antibody, and immunoreactive bands were visualised using enhanced chemiluminescence (ECL) reagent (Pierce). The immunoreactive bands corresponding to panVEGF and VEGF$_{xxx}$b in each treatment were quantified by ImageJ analysis and normalised to those of β-tubulin.

Statistical Analysis

Statistical analyses were carried out on raw data using the Friedman test (Dunnet post-test) and a p value of less than 0.5 was considered statistically significant. Values are expressed as means±SE (standard error). For all data n represents the number of independent RPE cell populations deriving from different donors.

Results

Figure 2:
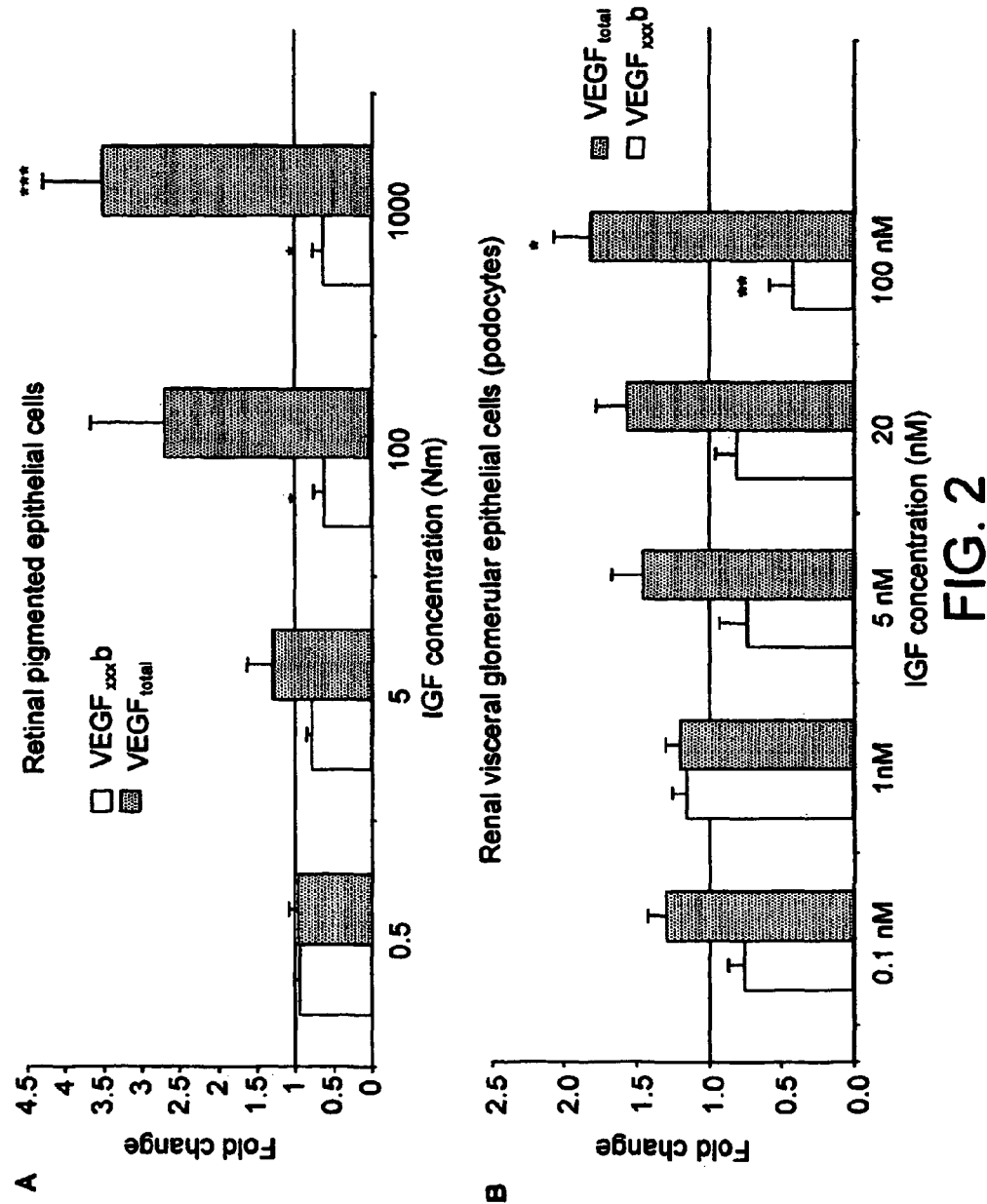
FIG. 2 shows the effect of IGF-1 on expression of $VEGF_{xxx}b$ and $VEGF_{xxx}$ proteins in (A) retinal pigmented epithelial (RPE) cells and (B) renal visceral glomerular epithelial cells (podocytes), details given in the legend and the discussion below.

IGF-1 and TNF-α Switch Splicing from Anti-Angiogenic to Pro-Angiogenic VEGF Isoforms Growth factors such as IGF-1, TNF-α and TGF-β$_1$ have previously been shown to increase total VEGF expression, but their effect on terminal exon splice site selection is not known (16, 18, 31, 34). In both epithelial cell types tested, RPE cells and podocytes, treatment with IGF-1 significantly upregulated total VEGF expression, but this upregulation was confined to the pro-angiogenic VEGF$_{xxx}$ isoforms (FIG. 2). In RPE cells IGF-1 resulted in a dose dependent increase in VEGF$_{total}$ from 217±112 pg/mg total protein to 1656±448 pg/mg protein at 100 nM IGF-1 (N=6, p<0.05 ANOVA, p<0.01 test for linear trend, FIG. 2A). This increase was due to an upregulation of VEGF$_{xxx}$ from 138±117 pg/mg protein to 1592 pg/mg protein, and a down-regulation of VEGF$_{xxx}$b from 78±12 pgmg protein to 64±14 pg/mg protein. Thus IGF induced a switch in expression such that the cells that were originally producing 80±32% of their VEGF as VEGF$_{xxx}$b, after IGF-1 treatment produced only 5±20% of their VEGF as VEGF$_{xxx}$b.

Figure 3:
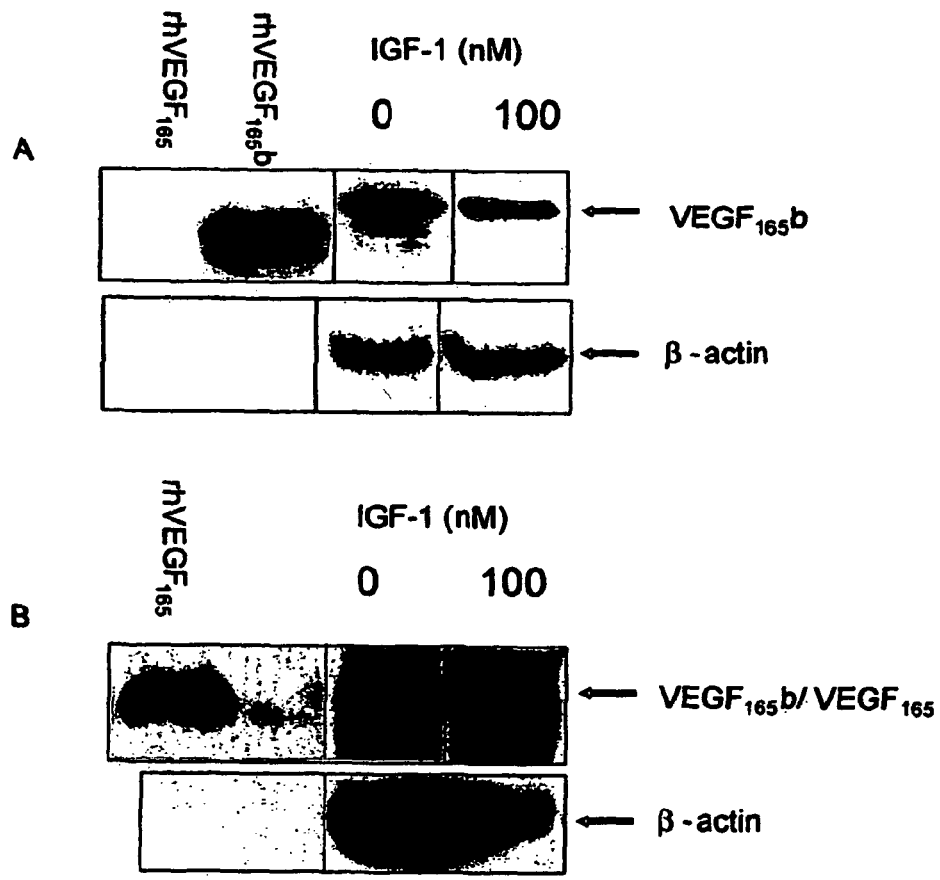
FIG. 3 shows the effect of IGF-1 on expression of (A) $VEGF_{165}b$ and (B) $VEGF_{165}$ in RPE cells, details given in the legend and the discussion below.

A similar effect was seen in another epithelial cell type, podocytes. These cells showed a decrease in VEGF$_{165}$b levels with a significant increase in total VEGF levels compared with control (FIG. 2B). To determine whether IGF-1 altered regulation of the VEGF$_{165}$ and VEGF$_{165}$b isoforms of their respective families, Western blotting was used. FIG. 3A shows that 100 nM IGF downregulated VEGF$_{165}$b in RPE cells (FIG. 3A), while resulting in an increase in total VEGF relative to loading control (β-actin, FIG. 3B). To determine whether switching of isoforms could be induced by other cytokines, RPE cells were incubated in 50 ng/ml TNF-α, and protein collected. TNFα induced an upregulation of VEGF$_{xxx}$ isoforms (from 182±83 pg/mg protein to 825±366 pg/mg protein (p<0.05, a mean increase of 4.5±2.0 fold (n=3). In contrast, 50 ng/ml TNF-α, significantly downregulated VEGF$_{xxx}$b isoforms (p<0.05) from 99±26 pg/mg to 42±13 pg/mg protein, a decrease of 46±3%.

TGF-β Switches Splicing to Anti-Angiogenic VEGF Isoforms

TGF-β1 has been shown to be involved in the regulation of splicing of other genes. (e.g. Tenascin (56), procollagen type II (50). Therefore we investigated whether TGF-β1 affected splicing of the VEGF mRNA.

Figure 4:
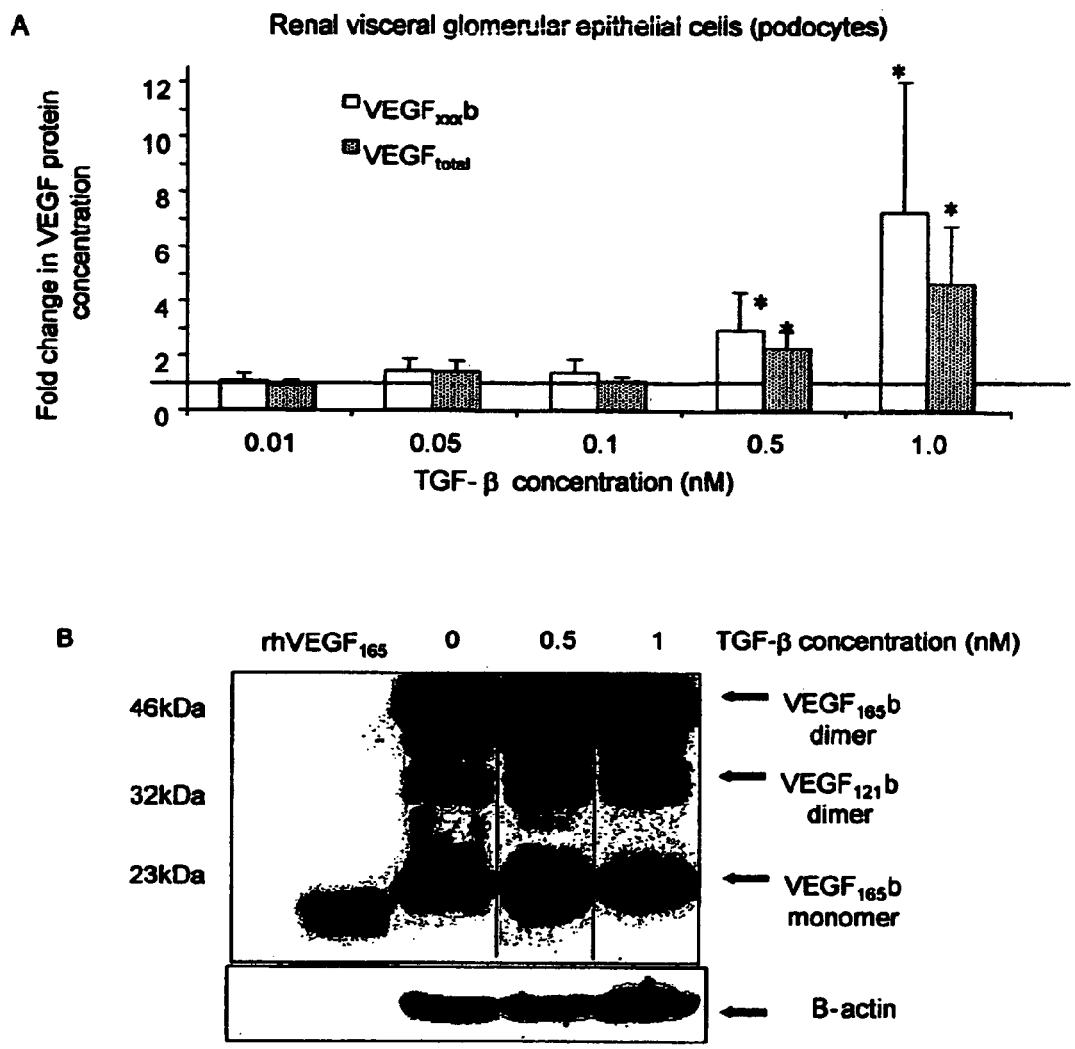
FIG. 4 shows the effect of TGF-β1 on expression of $VEGF_{xxx}b$ and $VEGF_{total}$ in podocytes, by (A) an ELISA assay of the podocyte cell lysate for the respective proteins and (B) a non-reducing Western Blot of the lysate, details given in the legend and the discussion below.

In contrast with IGF-1 and TNF-α, incubation with TGF-β1 at 0.5 nM and 1 nM for 48 h significantly increased the level of VEGF$_{xxx}$b protein (2.9±1.4 fold and 7.2±4.7 fold respectively, p<0.05 p<0.001 Dunnet's test) and total VEGF protein expression (2.25±0.65 and 4.63±0.61 fold respectively, p<0.001 Dunnet's. test, FIG. 4). Thus the VEGF$_{xxx}$ expression levels fell by 70±7% at 1 nM TGF-β. To determine whether the isoforms altered by TGF were the VEGF$_{165}$b and VEGF$_{165}$ isoforms, Western blotting was carried out on the cell lysate. FIG. 4B shows under lightly reducing conditions that both the VEGF$_{165}$b and VEGF$_{121}$b isoforms were upregulated by 0.5 and 1 nM TGF-β1. This blot also shows some evidence for upregulation of VEGF$_{121}$b.

Intracellular Mechanisms through which VEGF$_{165}$B Splicing is Regulated by Cytokines.

TGF-β1 has previously been shown to activate the p38-MAPK pathway (21), which has also been involved in mechanisms of regulation of splicing (e.g. 51, 32). To determine whether this pathway was involved in TGF-β mediated regulation of splicing, podocytes were incubated with the p38-MAPK inhibitor SB203580. Treatment with SB203580 significantly downregulated VEGF$_{165}$b expression from 850±50 pg/mg protein to 450±80 pg/mg (FIG. 5A), but did not increase the expression of VEGF$_{xxx}$ isoforms, which were below the detection limit in this experiment in either untreated or SB203820 treated cells. Furthermore, TGF-β did not increase expression of either VEGF$_{xxx}$b isoforms or VEGF$_{xxx}$ isoforms in the presence of SB203820 treated cells (FIG. 5B). Western blotting demonstrated that the principal isoform upregulated by TGF-β1 was VEGF$_{165}$b and this was inhibited by SB203820 (FIG. 5C).

To confirm that the changes seen by TGF-β1 were at the mRNA level, and the effect of inhibitors acted at the mRNA level, real time polymerase chain reaction (RT-PCR) was carried out using primers that detect both proximal splice isoforms (VEGF$_{xxx}$, 135 bp band) and distal spliced isoforms (VEGF$_{xxx}$b, 74 bp band). Amplification of mRNA from podocytes confirmed that TGF-β1 treatment (1 nM) resulted in an increase in relative density of the lower, VEGF$_{xxx}$b, band (FIG. 5A). This increase in intensity was inhibited by SB203820, but not by the p42/p44MAPK inhibitor PD98059. Interestingly, another kinase inhibitor, TG003, which inhibits the cdc42-like kinase clk1/sty, also inhibited the TGF-β1 mediated increased intensity of the VEGF$_{xxx}$b band. These findings were confirmed by Western blotting (FIG. 5B) and ELISA (FIG. 5C).

Transfection of RPE Cells with Known Splicing Factors Shows that Splicing Factors such as ASF/SF2, 9G8, and in Particular SRp55, Regulate C' Terminal Alternative Splicing of the VEGF Gene.

Figure 7:
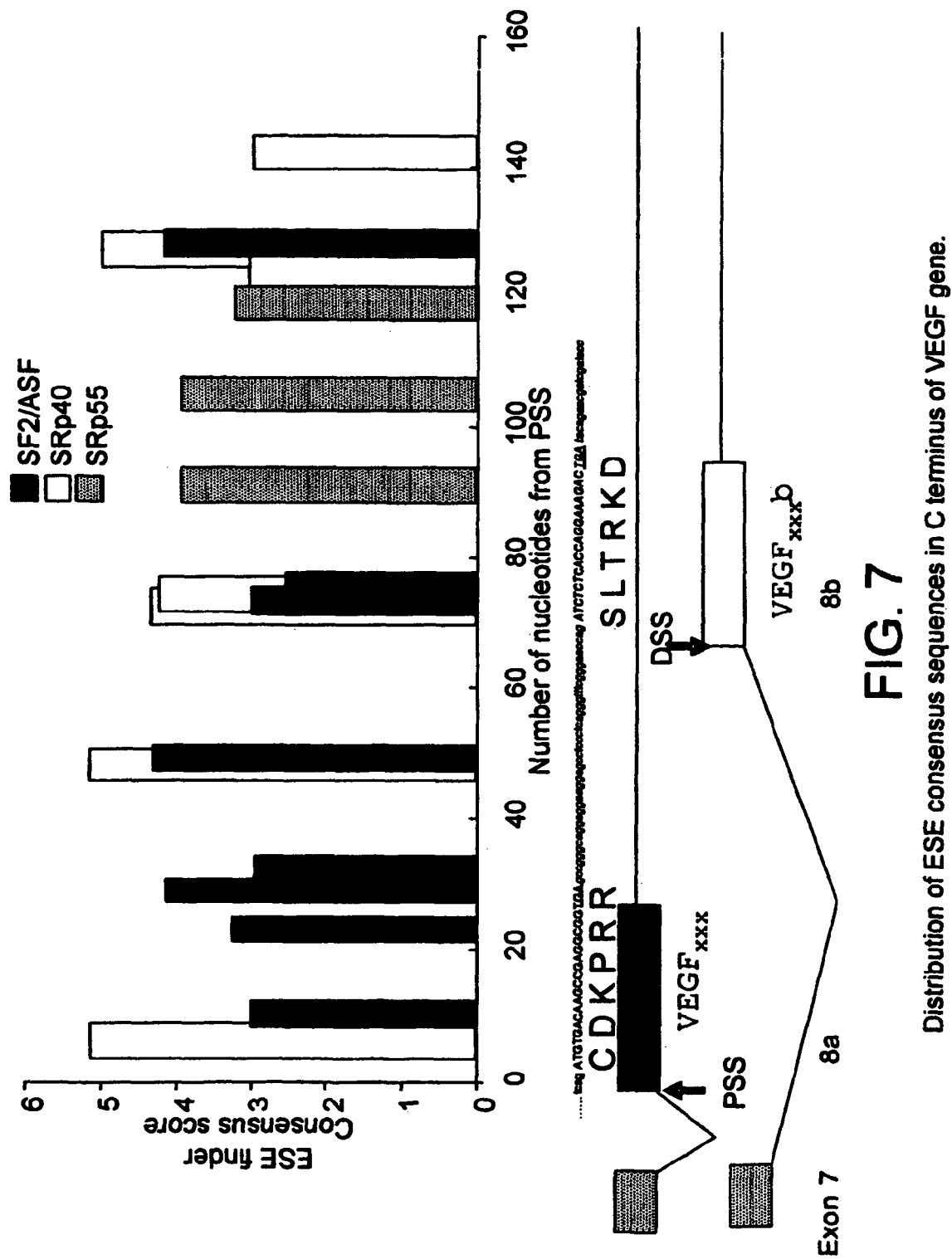
FIG. 7 shows the distribution of exon splicing enhancer (ESE) consensus sequences in the C terminus of the VEGF gene, details given in the legend and the discussion below.
Figure 9:
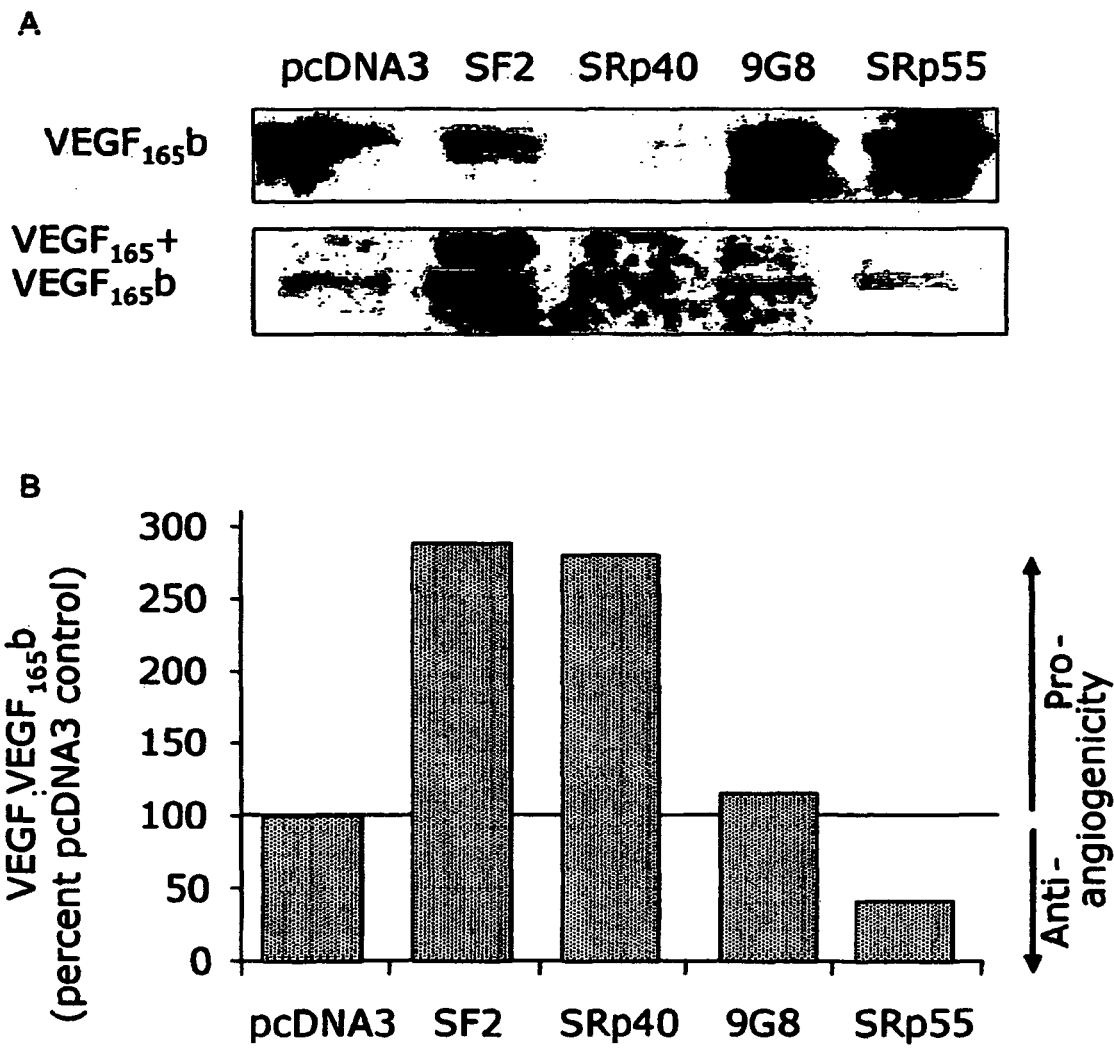
FIG. 9 shows (A) the Western Blots of FIG. 8A and additionally the pcDNA3 control, and (B) the ratio of $VEGF_{165}$ to $VEGF_{165}b$ compared with control, details given in the legend and the discussion below.
Figure 10:
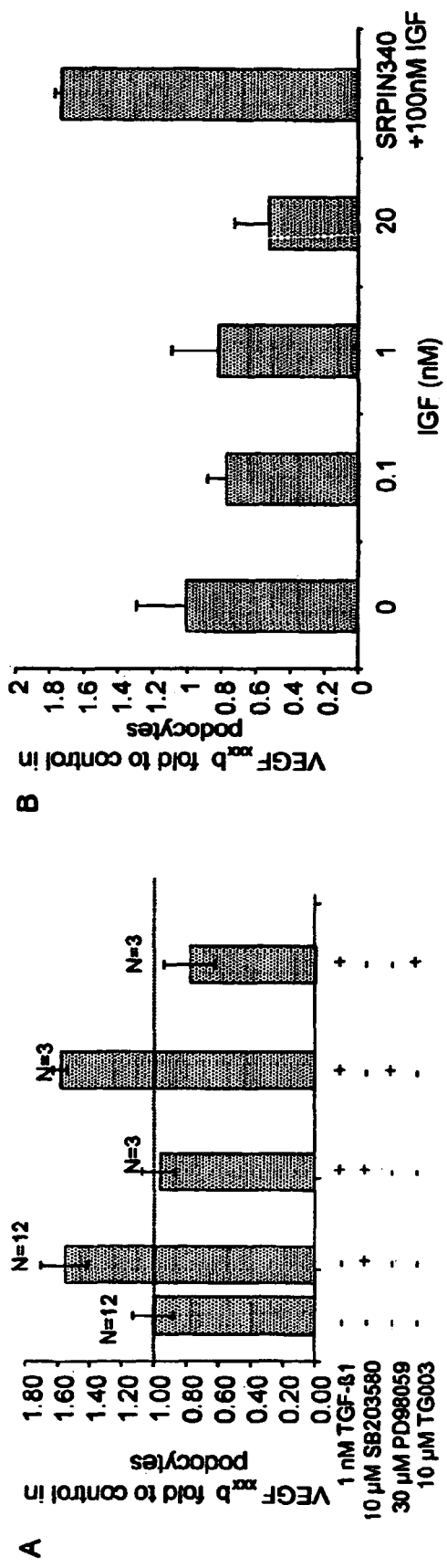
FIG. 10 shows (A) the production of $VEGF_{xxx}b$ compared with control in podocytes, by ELISA, following certain treatments shown in the Figure, (B) the production of $VEGF_{xxx}b$ compared with control in podocytes, by ELISA, following certain treatments of IGF at varying concentrations shown in the Figure, and following treatment with 100 nM IGF and Serpin 340, and (C) a scheme showing the apparent activation and inhibition effects leading to the observed splicing selection patterns, details given in the legend and the discussion below.

Clk/Sty has been shown to result in phosphorylation of three known splicing factors Alternative Splicing Factor/Splicing Factor 2 (ASF/SF2), SRp55 and SRp40. The distribution of known ESE consensus sequences for these splicing factors in the C terminus of VEGF gene, generated from ESEFinder are shown in FIG. 7. There is a strong cluster of SRp55 binding sites just distal to the distal splice sites, and a strong cluster of ASF/SF2 and SRp40 sites adjacent to the proximal splice site. To determine whether these splicing factors can regulate VEGF terminal exon splice site selection, we transfected retinal pigmented epithelial (RPE) cells with splicing factor cDNAs in pcDNA3 vector, and total protein and conditioned medium collected and analysed by Western Blotting (densitometrically, FIG. 8A) and ELISA (FIGS. 8B, 8C, 8D) respectively. ASF/SF2 did not significantly increase the amount of VEGF$_{165}$b in the cell lysate, but increased the amount of VEGF$_{total}$ (mean±SEM, n=3 41.4%±6.9%, p<0.05, FIG. 8A). The SR protein 9G8 significantly increased both VEGF$_{xxx}$b (78.6%±4.7%, p<0.01) and VEGF$_{total}$ (13.7%±2.9%, p<0.05) levels in the cell lysate (FIG. 8A). SRp55 increased the amount of VEGF$_{xxx}$b (104.5%±18.0%, p<0.01) but did not increase VEGF$_{total}$ (e.g. FIG. 8A). SRp40 did not alter the amount of VEGF$_{total}$ or VEGF$_{xxx}$b protein (FIG. 8A). To determine whether secreted VEGF levels were similarly altered, cell supernatant was also assayed by ELISA. Compared with untreated RPE cells ASF/SF2, SRp55 and SRp40 appeared to decrease the amount of VEGF$_{total}$ protein detected in the medium by 12.8%±4.8%, 70.9%±3.6%, and 34.1%±4.6%, respectively (FIG. 8B). 9G8 did not affect the level of VEGF$_{total}$ (FIG. 8B). In contrast SRp55 overexpression did significantly increase the concentration of VEGF$_{xxx}$b in the media. To determine the effect of these changes on overall relative expression levels, the concentration of VEGF$_{xxx}$b to VEGF$_{total}$ was calculated in the media (FIG. 8D). It can be seen that SRp55 results in a significant switch in splicing towards the anti-angiogenic VEGF isoforms. These results indicate that that splicing factors such as ASF/SF2, 9G8, and in particular SRp55, regulate C' terminal alternative splicing of the VEGF gene (FIGS. 9 and 10).

The balance of the VEGF$_{xxx}$ (pro-angiogenic) and VEGF$_{xxx}$b (anti-angiogenic) families, derived from the same gene, thus seems to play an important role in the control of angiogenesis in health and an imbalance may underpin pathological angiogenesis (FIG. 10C). Understanding the properties, expression and control of the VEGF$_{xxx}$b family may therefore have wide-ranging therapeutic implications in diseases as diverse as cancer, vascular disease, arthritis, diabetes, renal disease and psoriasis.

Therapies that inhibit angiogenesis have been approved after major phase III clinical trials in cancer and AMD (19, 25). Recent phase II and III trials show significant efficacy of anti-VEGF therapies in colorectal (25, 35), and renal cell carcinoma (55) and in age-related macular degeneration (14).

Our work, described herein, on alternate splicing of the VEGF gene resulting in anti-angiogenic as well as pro-angiogenic isoforms indicates that controlling and understanding the balance of each isoform family may be essential to define the optimal therapeutic option and dosing. We have found splicing factors (particularly SRp55) and growth factors (especially TGF-β) that could preferentially select for distal C'terminal splicing.

Figure 11:
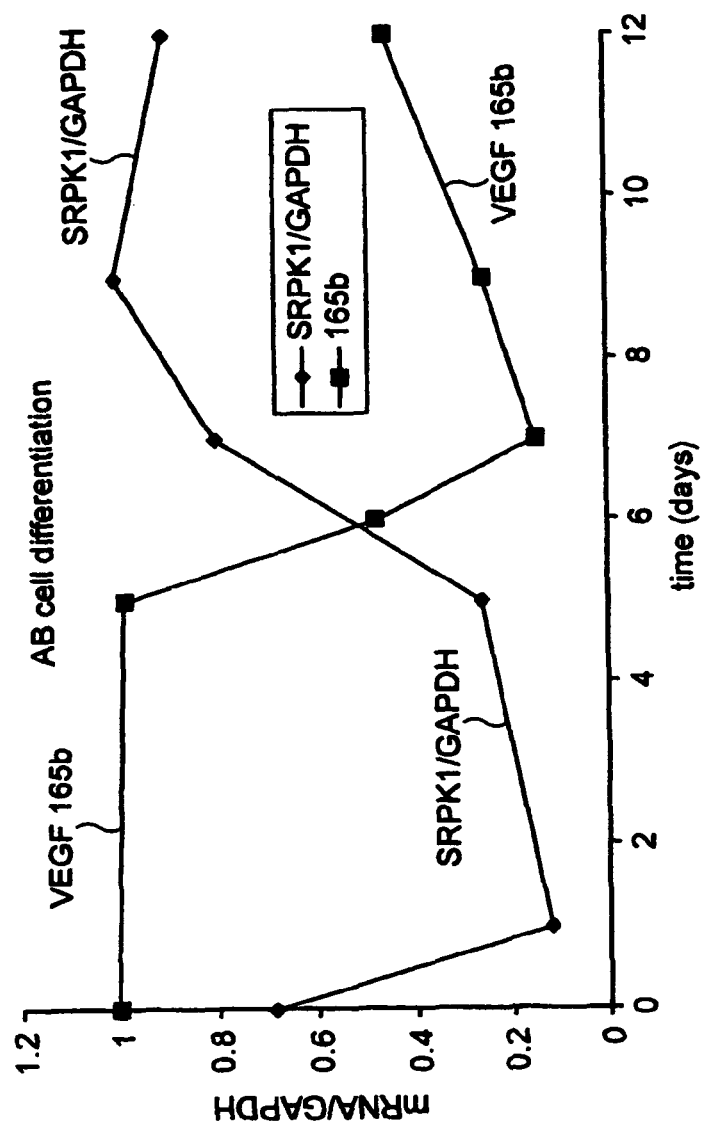
FIG. 11 shows the results of RT-PCR analysis of the levels of SRPK1 and $VEGF_{165}b$ in podocytes undergoing differentiation, details given in the legend and the discussion below.

Splicing factors are regulated by specific signalling molecules, either directly (SR protein kinases such as clk1, or SRPKs), or indirectly (MAPKs and PKC). SRPKs phosphorylate SF2/ASF, which favours proximal splicing (FIG. 10C). Semi-quantitative RT-PCR for SRPK1 shows that SRPK, implicated in tumour progression (20) is downregulated during differentiation of podocytes, and that this downregulation mimics the alteration in splicing from VEGF$_{165}$ to VEGF$_{165}$b (FIG. 11).

Figure 12:
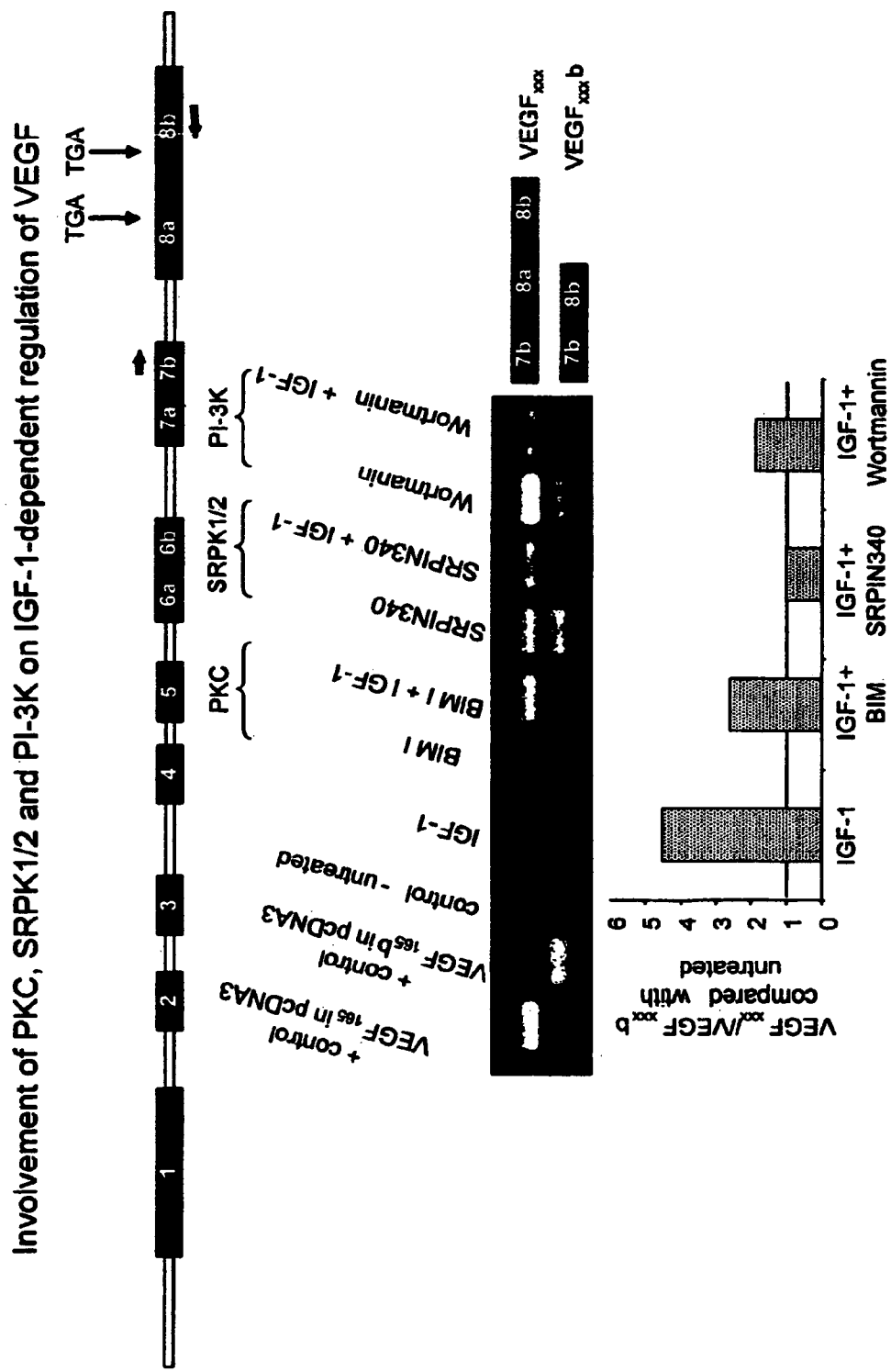
FIG. 12 shows the results of RT-PCR analysis of the extent of proximal splicing in podocytes after treatment with IGF, details given in the legend and the discussion below.
Figure 13:
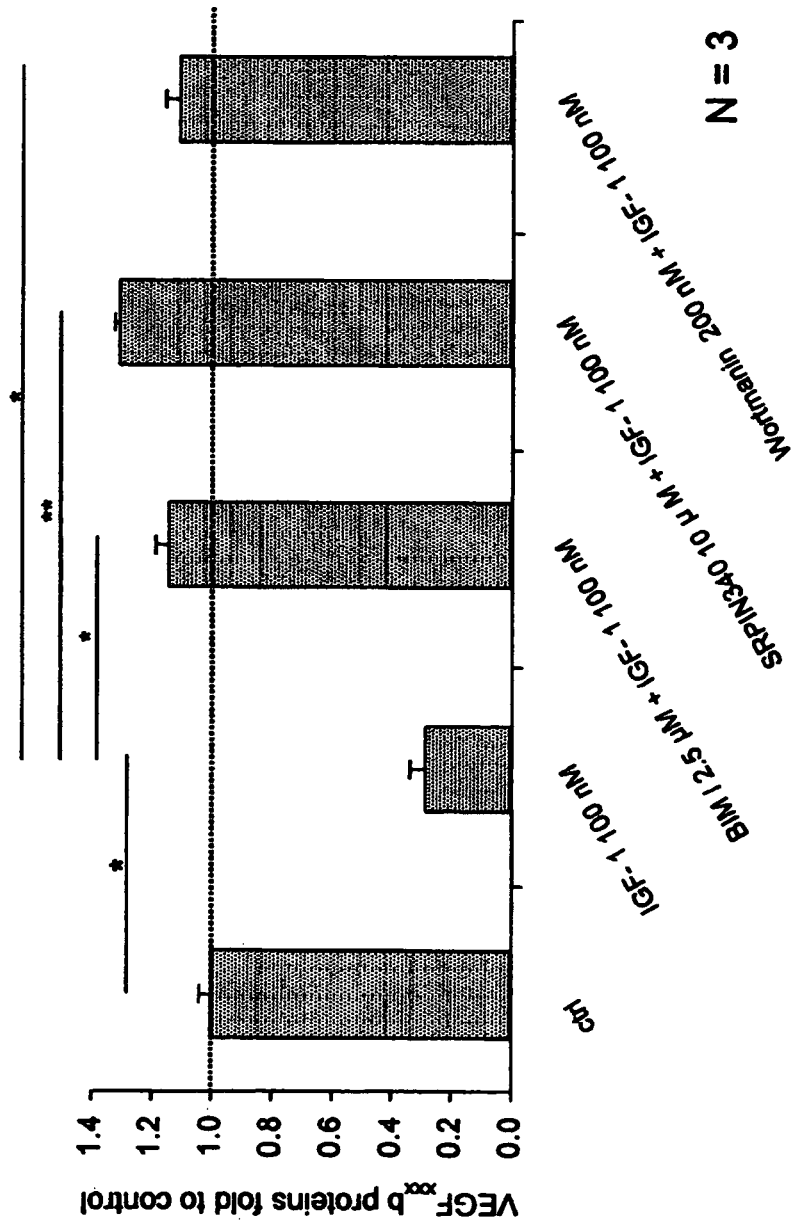
FIG. 13 shows the results of ELISA analysis of the extent of proximal splicing in podocytes after treatment with IGF, details given in the legend and the discussion below.

Treatment of podocytes with IGF increases PSS as evidenced by RT-PCR and ELISA. This increase is inhibited by the PKC inhibitor BIM and the SR protein kinase inhibitor SERPIN340 (FIGS. 12 and 13).

SRp55 regulates VEGF splice selection in exon 8. SRp55-transfected podocytes show a very slight increase in VEGF$_{165}$b expression in comparison to a highly increased SRp55 expression. shRNA (short hairpin interfering RNA) targeting SRp55 downregulated both SRp55 and VEGF$_{165}$b expression (FIG. 14A, immunoblot is the left portion of the Figure; quantification of the shRNA interference is the right portion of the Figure). RNA was generated by in vitro transcription from three constructs ending with the MS2 RNA binding sequence containing three recognition sequences for the maltose binding protein (MBP). Construct X contained 88 nucleotides around exon 8b open reading frame. Construct Y contained a deletion of the 35 bp downstream of the stop codon. Construct Z contained only the MS2 sequence. These RNAs were incubated with nuclear extract from HEK293 cells (positive control) and MS2 and run on a maltose column. Maltose binds to MS2-MBP protein. Bound and unbound fractions were collected and immunoblotted for SRp55. A 55 kDa band was seen in the fraction bound to construct X RNA, and in nuclear extract run as a positive control, but not in the other constructs, demonstrating that SRp55 bound to the 35 bp region downstream of the stop codon in exon 8b. The unbound fraction contained SRp55 in all samples (FIG. 14B, upper portion is a diagram showing the arrangements of coding regions of exon 8 in the three constructs; lower portion shows the immunoblots of the bound (upper) and unbound (lower) fractions.

Colon carcinoma cells (10C and LS174t) that normally express less (10C) or little VEGF$_{165}$b were transfected with empty vector or TIA-1 cDNA. TIA-1 is an RNA-binding protein previously shown {unpublished data} to be mutated in 10C cells. RNA was extracted and subjected to PCR using forward primers in exon 7 and reverse primers in the 3'UTR of the VEGF mRNA (FIG. 15; the lower band is a result of distal splice site (DSS) selection (leading to VEGF$_{165}$b) and the upper band is the result of proximal splice site selection (PSS) leading to VEGF$_{165}$). This indicates that TIA-1 activation may be a potential anti-angiogenic therapeutic strategy.

Morpholino (MO) treatment of HEK cells shows that the ratio of expressed VEGF$_{165}$b to VEGF$_{165}$ can be dose-dependently controlled to reduce (FIG. 17) or increase (FIG. 18) the ratio, depending on whether the morpholino targets the DSS (FIG. 17) or the PSS (FIG. 18). In each Figure, the top portion (A) shows the sequence diagram showing the morpholino location (see FIG. 16 for sequence details), the centre portion (B) shows the RT-PCR bands showing the effect of increasing the morpholino concentration, and the lower portion (C) shows the quantification of the VEGF$_{165}$b: VEGF$_{165}$ ratio by densitometry.

Immunohistochemistry studies have been conducted on tissues of human embryos to show that in human embryos the expression of VEGF$_{xxx}$b isoforms is widespread (FIG. 19). VEGF$_{165}$b is seen in the photomicrographs to be highly expressed in the spinal cord, particularly in the ventral horn and the dorsal root ganglion. It is expressed in the endothelial cells, for example in the developing jugular vein and carotid artery, in the brain, though not uniformly expressed, and in the lymphoid tissue. Interestingly, its expression is upregulated in skin between 8 and 16 weeks of development. It is expressed in osteoblasts and periosteum of developing bone, but not in chondroblasts at this stage. It is widely and strongly expressed in epithelial cells, for example in the oesophagus and trachea, as well as in specific areas of the CNS such as the choroid plexus and the developing eye. The widespread distribution of VEGF$_{165}$b expression supports the principles underlying the present invention, namely that splice site selection can offer substantial clinical benefits in the pro- and anti-angiogenic treatment of tissues in a wide variety of sites in the body, and the control systems enabled by the present invention will be expected to be functional in a wide range of tissues.

INDUSTRIAL APPLICABILITY

The present invention provides agents and targets for the manipulation of the splicing control, in conjunction with unaltered promoter activity, in order to promote distal (exon 8b—anti-angiogenic), rather than proximal (exon 8a—pro-angiogenic) splice site selection in expression of the VEGF gene in mammals, particularly humans.

This novel and unpredictable finding enables a therapy that, in the cancer example, would encourage the tumour to switch off its own nutrient supply. Indeed, the more hypoxic the tumor became, the more effective this therapeutic switch might be, in view of the known effects of hypoxia in the transcriptional regulation of VEGF gene expression (47).

In particular, IGF, and TNF-α, treatment altered expression to favour PSS (VEGF$_{xxx}$) whereas TGF-β1, favoured DSS, increasing VEGF$_{xxx}$b levels. This TGF-β1 induced DSS was prevented by inhibition of p38MAPK, and by inhibition of the splicing factor kinase clk/sty, but not by inhibition of ERK1/2. Clk/sty has been shown to phosphorylate SR protein splicing factors such as ASF/SF2, SRp40 and Srp55. To determine whether SR splicing factors could alter VEGF splicing, they were over-expressed in epithelial cells, and differential isoform production assessed. ASF/SF2, and Srp40 both favoured PSS, whereas SRp55 upregulated VEGF$_{xxx}$b isoforms relative to VEGF$_{xxx}$ (DSS) in a manner that was inhibited by siRNA targeting SRp55. The PKC inhibitor BIM, as well as TIA-1, also favoured VEGF$_{165}$b. These results identify regulation of splicing by growth and splice factors as a key event in determining the relative pro-versus anti-angiogenic expression of VEGF isoforms, and suggest that p38MAPK-clk/st kinases may be responsible for the TGF-β1-induced distal splice site selection.

These findings further enable a method for facilitating diagnosis and/or prognosis of conditions having an aspect relating to angiogenesis, and for enabling the subsequent treatment of those conditions to be tailored to the underlying biochemistry of the condition in the subject.

The present invention also provides a rationale for the development of diagnostic agents and methods in relation to the susceptibility of a potential lesion or condition to a pro- or anti-angiogenic therapeutic strategy, since we have shown that the anti- to pro-angiogenic switch is heterogeneous in patients with the same clinical condition, e.g. diabetic retinopathy and colonic carcinoma. Detailed analysis of the balance of VEGF$_{xxx}$/VEGF$_{xxx}$b isoform expression may predict susceptibility of a lesion or condition to treatment, or to a particular treatment, or allow the specific tailoring of treatment for the individual patient increasing therapeutic effectiveness and reducing side effects.

REFERENCES

1. Asano-Kato N, Fukagawa K, Okada N, Kawakita T, Takano Y, Dogru M, Tsubota K, and Fujishima H. TGF-beta1, IL-1beta, and Th2 cytokines stimulate vascular endothelial growth factor production from conjunctival fibroblasts. *Exp Eye Res* 80: 555-560, 2005.
2. Bates D O, Cui T G, Doughty J M, Winkler M, Sugiono M, Shields J D, Peat D, Gillatt D, and Harper S J. VEGF165b, an inhibitory splice variant of vascular endothelial growth factor, is down-regulated in renal cell carcinoma. *Cancer Res* 62: 4123-4131., 2002.
3. Bates D O, Macmillan P P, Manjaly J G, Qiu Y, Hudson S J, Bevan H S, Hunter A J, Soothill P W, Read M, Donaldson L F, and Harper S J. The endogenous anti-angiogenic family of splice variants of VEGF, VEGF xxxb, are down-regulated in pre-eclamptic placentae at term. *Clin Sci (Lond)*, 2006.
4. Bevan H S, Harper S J, and Bates D O. VEGF165b, the anti-angiogenic isoform of VEGF, differentially stimulates VEGFR2, MAPK and Akt phosphorylation in endothelial cells. *submitted*, 2006.
5. Caceres J F and Kornblihtt A R. Alternative splicing: multiple control mechanisms and involvement in human disease. *Trends Genet* 18: 186-193., 2002.
6. Carmeliet P. VEGF gene therapy: stimulating angiogenesis or angioma-genesis? *Nat Med* 6: 1102-1103, 2000.
7. Celletti F L, Waugh J M, Amabile P G, Brendolan A, Hilfiker P R, and Dake M D. Vascular endothelial growth factor enhances atherosclerotic plaque progression. *Nat Med* 7: 425-429., 2001.
8. Charnock-Jones D S, Macpherson A M, Archer D F, Leslie S, Makkink W K, Sharkey A M, and Smith S K. The effect of progestins on vascular endothelial growth factor, oestrogen receptor and progesterone receptor immunoreactivity and endothelial cell density in human endometrium. *Hum Reprod* 15 Suppl 3: 85-95, 2000.
9. Cohen C D, Doran P P, Blattner S M, Merkle M, Wang G Q, Schmid H, Mathieson P W, Saleem M A, Henger A, Rastaldi M P, and Kretzler M. Sam68-Like Mammalian Protein 2, Identified by Digital Differential Display as Expressed by Podocytes, Is Induced in Proteinuria and Involved in Splice Site Selection of Vascular Endothelial Growth Factor. *J Am Soc Nephrol*, 2005.
10. Cramer P, Caceres J F, Cazalla D, Kadener S, Muro A F, Baralle F E, and Kornblihtt A R. Coupling of transcription with alternative splicing: RNA pol II promoters modulate SF2/ASF and 9G8 effects on an exonic splicing enhancer. *Mol Cell* 4: 251-258., 1999.
11. Cui T G, Foster R R, Saleem M, Mathieson P W, Gillatt D A, Bates D O, and Harper S J. Differentiated human podocytes endogenously express an inhibitory isoform of vascular endothelial growth factor (VEGF165b) mRNA and protein. *Am J Physiol Renal Physiol* 286: F767-773, 2004.
12. Dowhan D H, Hong E P, Auboeuf D, Dennis A P, Wilson M M, Berget S M, and O'Malley B W. Steroid hormone receptor coactivation and alternative RNA splicing by U2AF65-related proteins CAPERalpha and CAPERbeta. *Mol Cell* 17: 429-439, 2005.
13. Endo H, Matsuda C, and Kagawa Y. Exclusion of an alternatively spliced exon in human ATP synthase gamma-subunit pre-mRNA requires de novo protein synthesis. *J Biol Chem* 269: 12488-12493., 1994.
14. Eyetech. Anti-vascular endothelial growth factor therapy for subfoveal choroidal neovascularization secondary to age-related macular degeneration: phase II study results. *Opthalmology* 110: 979-986., 2003.
15. Ferrara N and Davis-Smyth T. The biology of vascular endothelial growth factor. *Endocr Rev* 18: 4-25., 1997.
16. Finkenzeller G, Sparacio A, Technau A, Marme D, and Siemeister G. Sp1 recognition sites in the proximal promoter of the human vascular endothelial growth factor gene are essential for platelet-derived growth factor-induced gene expression. *Oncogene* 15: 669-676., 1997.
17. Folkman J. Tumor angiogenesis. *Adv Cancer Res* 43: 175-203, 1985.
18. Goad D L, Rubin J, Wang H, Tashjian A H, Jr., and Patterson C. Enhanced expression of vascular endothelial growth factor in human SaOS-2 osteoblast-like cells and murine osteoblasts induced by insulin-like growth factor I. *Endocrinology* 137: 2262-2268., 1996.
19. Gragoudas E S, Adamis A P, Cunningham E T, Jr., Feinsod M, and Guyer D R. Pegaptanib for neovascular age-related macular degeneration. *N Engl J Med* 351: 2805-2816, 2004.
20. Hayes G M, Carrigan P E, Beck A M, and Miller L J. Targeting the RNA splicing machinery as a novel treatment strategy for pancreatic carcinoma. *Cancer Res* 66: 3819-3827, 2006.
21. Herrera B, Fernandez M, Roncero C, Ventura J J, Porras A, Valladares A, Benito M, and Fabregat I. Activation of p38MAPK by TGF-beta in fetal rat hepatocytes requires radical oxygen production, but is dispensable for cell death. *Febs Lett* 499: 225-229, 2001.
22. Hertel K J, Lynch K W, and Maniatis T. Common themes in the function of transcription and splicing enhancers. *Curr Opin Cell Biol* 9: 350-357., 1997.
23. Hirose Y, Tacke R, and Manley J L. Phosphorylated RNA polymerase II stimulates pre-mRNA splicing. *Genes Dev* 13: 1234-1239., 1999.
24. Houck K A, Ferrara N, Winer J, Cachianes G, Li B, and Leung D W. The vascular endothelial growth factor family: identification of a fourth molecular species and characterization of alternative splicing of RNA. *Mol Endocrinol* 5: 1806-1814, 1991.
25. Hurwitz H, Fehrenbacher L, Novotny W, Cartwright T, Hainsworth J, Heim W, Berlin J, Baron A, Griffing S, Holmgren E, Ferrara N, Fyfe G, Rogers B, Ross R, and Kabbinavar F. Bevacizumab plus irinotecan, fluorouracil, and leucovorin for metastatic colorectal cancer. *N Engl J Med* 350: 2335-2342, 2004.
26. Idriss H, Kumar A, Casas-Finet J R, Guo H, Damuni Z, and Wilson S H. Regulation of in vitro nucleic acid strand annealing activity of heterogeneous nuclear ribonucleoprotein protein A1 by reversible phosphorylation. *Biochemistry* 33: 11382-11390., 1994.
27. Kalnina Z, Zayakin P, Silina K, and Line A. Alterations of pre-mRNA splicing in cancer. *Genes Chromosomes Cancer* 42: 342-357, 2005.
28. Koenigsberger C, Chicca J J, 2nd, Amoureux M C, Edelman G M, and Jones F S. Differential regulation by multiple promoters of the gene encoding the neuron-restrictive silencer factor. *Proc Natl Acad Sci USA* 97: 2291-2296., 2000.
29. Kotsuji-Maruyama T, Imakado S, Kawachi Y, and Otsuka F. PDGF-BB induces MAP kinase phosphorylation and VEGF expression in neurofibroma-derived cultured cells from patients with neurofibromatosis 1. *J Dermatol* 29: 713-717, 2002.
30. Li H, Yonekura H, Kim C H, Sakurai S, Yamamoto Y, Takiya T, Futo S, Watanabe T, and Yamamoto H. Possible participation of pICln in the regulation of angiogenesis through alternative splicing of vascular endothelial growth factor receptor mRNAs. *Endothelium* 11: 293-300, 2004.
31. Li J, Perrella M A, Tsai J C, Yet S F, Hsieh C M, Yoshizumi M, Patterson C, Endege W O, Zhou F, and Lee M E. Induction of vascular endothelial growth factor gene expression by interleukin-1 beta in rat aortic smooth muscle cells. *J Biol Chem* 270: 308-312., 1995.
32. Lin J C, Hsu M, and Tarn W Y. Cell stress modulates the function of splicing regulatory protein RBM4 in translation control. *Proc Natl Acad Sci USA* 104: 2235-2240, 2007.
33. Lynch K W and Maniatis T. Assembly of specific SR protein complexes on distinct regulatory elements of the Drosophila doublesex splicing enhancer. *Genes Dev* 10: 2089-2101., 1996.
34. Matsumoto K, Ohi H, and Kanmatsuse K. Interleukin 10 and interleukin 13 synergize to inhibit vascular permeability factor release by peripheral blood mononuclear cells from patients with lipoid nephrosis. *Nephron* 77: 212-218., 1997.
35. McCarthy M. Antiangiogenesis drug promising for metastatic colorectal cancer. *Lancet* 361: 1959., 2003.
36. Misteli T, Caceres J F, and Spector D L. The dynamics of a pre-mRNA splicing factor in living cells. *Nature* 387: 523-527., 1997.
37. Mukhopadhyay D, Tsiokas L, Zhou X M, Foster D, Brugge J S, and Sukhatme V P. Hypoxic induction of human vascular endothelial growth factor expression through c-Src activation. *Nature* 375: 577-581, 1995.
38. Neufeld G, Cohen T, Gengrinovitch S, and Poltorak Z. Vascular endothelial growth factor (VEGF) and its receptors. *Faseb J* 13: 9-22, 1999.
39. Neufeld G, Cohen T, GitayGoren H, Poltorak Z, Tessler S, Sharon R, Gengrinovitch S, and Levi B Z. Similarities and differences between the vascular endothelial growth factor (VEGF) splice variants. *Cancer and Metastasis Reviews* 15: 153-158, 1996.
40. Patterson C, Perrella M A, Endege W O, Yoshizumi M, Lee M E, and Haber E. Downregulation of vascular endothelial growth factor receptors by tumor necrosis factor-alpha in cultured human vascular endothelial cells. *J Clin Invest* 98: 490-496., 1996.
41. Perkett E A and Klekamp J G. Vascular endothelial growth factor expression is decreased in rat lung following exposure to 24 or 48 hours of hyperoxia: implications for endothelial cell survival. *Chest* 114: 52S-53S., 1998.
42. Perrin R M, Konopatskaya O, Qiu Y, Harper S, Bates D O, and Churchill A J. Diabetic retinopathy is associated with a switch in splicing from anti- to pro-angiogenic isoforms of vascular endothelial growth factor. *Diabetologia* 48: 2422-2427, 2005.
43. Pertovaara L, Kaipainen A, Mustonen T, Orpana A, Ferrara N, Saksela O, and Alitalo K. Vascular endothelial growth factor is induced in response to transforming growth factor-beta in fibroblastic and epithelial cells. *J Biol Chem* 269: 6271-6274., 1994.
44. Pritchard-Jones R O, Dunn D B A, Qiu Y, Rigby H, Orlando A, Harper S J, and Bates D O. Immunohistochemical expression of $VEGF_{xxx}b$ predicts metastasis in primary melanoma. *J Pathology*, 2006.
45. Rak J, Mitsuhashi Y, Bayko L, Filmus J, Shirasawa S, Sasazuki T, and Kerbel R S. Mutant ras oncogenes upregulate VEGF/VPF expression: implications for induction and inhibition of tumor angiogenesis. *Cancer Res* 55: 4575-4580, 1995.
46. Saleem M A, O'Hare M J, Reiser J, Coward R J, Inward C D, Farren T, Xing C Y, Ni L, Mathieson P W, and Mundel P. A conditionally immortalized human podocyte cell line demonstrating nephrin and podocin expression. *J Am Soc Nephrol* 13: 630-638., 2002.
47. Shweiki D, Itin A, Soffer D, and Keshet E. Vascular endothelial growth factor induced by hypoxia may mediate hypoxia-initiated angiogenesis. *Nature* 359: 843-845., 1992.
48. Smith C W. Alternative splicing—when two's a crowd. *Cell* 123: 1-3, 2005.
49. Sone H, Kawakami Y, Okuda Y, Kondo S, Hanatani M, Suzuki H, and Yamashita K. Vascular endothelial growth factor is induced by long-term high glucose concentration and up-regulated by acute glucose deprivation in cultured bovine retinal pigmented epithelial cells. *Biochem Biophys Res Commun* 221: 193-198., 1996.
50. Valcourt U, Gouttenoire J, Aubert-Foucher E, Herbage D, and Mallein-Gerin F. Alternative splicing of type II procollagen pre-mRNA in chondrocytes is oppositely regulated by BMP-2 and TGF-beta1. *Febs Lett* 545: 115-119, 2003.
51. van der Houven van Oordt W, Diaz-Meco M T, Lozano J, Krainer A R, Moscat J, and Caceres J F. The MHK(3/6)-p38-signaling cascade alters the subcellular distribution of hnRNP A1 and modulates alternative splicing regulation. *J Cell Biol* 149: 307-316, 2000.
52. Varey A H R, Rennel E S, Qiu Y, Bevan H S, Perrin R M, Raffy S, Dixon A R, Paraskeva C, Zaccheo O, Hassan A B, Harper S J, and Bates D O. $VEGF_{165}b$, an antiangiogenic VEGF-A isoform, binds and inhibits bevacizumab treatment in experimental colorectal carcinoma: balance of pro- and antiangiogenic VEGF-A isoforms has implications for therapy. *Br J Cancer* In Press 2008
53. Venables J P. Aberrant and alternative splicing in cancer. *Cancer Res* 64: 7647-7654, 2004.
54. Woolard J, Wang W Y, Bevan H S, Qiu Y, Morbidelli L, Pritchard-Jones R O, Cui T G, Sugiono M, Waine E, Perrin R, Foster R, Digby-Bell J, Shields J D, Whittles C E, Mushens R E, Gillatt D A, Ziche M, Harper S J, and Bates D O. VEGF165b, an inhibitory vascular endothelial growth factor splice variant: mechanism of action, in vivo effect on angiogenesis and endogenous protein expression. *Cancer Res* 64: 7822-7835, 2004.
55. Yang J C, Haworth L, Sherry R M, Hwu P, Schwartzentruber D J, Topalian S L, Steinberg S M, Chen H X, and Rosenberg S A. A randomized trial of bevacizumab, an anti-vascular endothelial growth factor antibody, for metastatic renal cancer. *N Engl J Med* 349: 427-434., 2003.
56. Zhao Y and Young S L. TGF-beta regulates expression of tenascin alternative-splicing isoforms in fetal rat lung. *Am J Physiol* 268: L173-180, 1995.

The invention claimed is:

1. A method of treatment of a disease or disorder associated with abnormal angiogenesis or abnormal over-production of pro-angiogenic VEGF isoforms in a mammalian subject, comprising:
   administering to the mammalian subject one or more splicing controlling agents which favour distal splice site (DSS) splicing, for site-specific control of alternative splicing during processing of VEGF pre-mRNA from the C terminal exon of the VEGF gene,
   wherein the one or more splicing controlling agents are selected from SRPIN 340 or functionally active analogs thereof;
   and any combination thereof.

2. The method of claim 1, wherein the method comprises administering to the mammalian subject a composition comprising the one or more splicing controlling agents and a physiologically acceptable carrier, diluent or excipient.

3. The method of claim 1, wherein the disease or disorder is selected from vascular disease, malignant and benign neoplasia, tumor metastasis, inflammatory disorders, diabetes, diabetic retinopathy and other complications of diabetes, trachoma, retrolental hyperplasia, neovascular glaucoma, age-related macular degeneration, haemangioma, immune rejection of implanted corneal tissue, corneal angiogenesis associated with ocular injury or infection, Osler-Webber Syndrome, myocardial angiogenesis, wound granulation, telangiectasia, hemophiliac joints, angiofibroma, telangiectasia psoriasis scleroderma, pyogenic granuloma, coronary collaterals, ischemic limb angiogenesis, rubeosis, obesity, arthritis, hematopoieses, vasculogenesis, gingivitis, atherosclerosis, endometriosis, neointimal hyperplasia, psoriasis, hirsutism and proliferative retinopathy.

4. The method of claim 1, wherein the disease or disorder is age-related macular degeneration, malignant neoplasia, tumor metastasis or diabetic retinopathy.

5. A method of treating age-related macular degeneration, malignant neoplasia, tumor metastasis or diabetic retinopathy in a mammalian subject, comprising:
   administering to the mammalian subject a composition comprising one or more splicing controlling agents selected from SRPIN 340 or functionally active analogs thereof;
   in combination with a physiologically acceptable carrier, diluent or excipient.

* * * * *